(12) United States Patent
Leclerc et al.

(10) Patent No.: US 7,071,221 B2
(45) Date of Patent: Jul. 4, 2006

(54) HETEROCYCLIC OXIME COMPOUNDS

(75) Inventors: Véronique Leclerc, Lille (FR); Sylvie Pailloux, Poitiers (FR); Pascal Carato, Lille (FR); Carine Introvigne, Chaptelat (FR); Nicolas Lebegue, Wignehies (FR); Pascal Berthelot, Haubourdin (FR); Catherine Dacquet, Paris (FR); Jean Albert Boutin, Suresnes (FR); Daniel Henri Caignard, Le Pecq (FR); Pierre Renard, Le Chesnay (FR)

(73) Assignee: Les Laboratoires Servier, Courbevoie (FR)

( * ) Notice: Subject to any disclaimer, the term of this patent is extended or adjusted under 35 U.S.C. 154(b) by 44 days.

(21) Appl. No.: 10/902,345

(22) Filed: Jul. 29, 2004

(65) Prior Publication Data

US 2005/0026973 A1 Feb. 3, 2005

(51) Int. Cl.
*A61K 31/428* (2006.01)
*A61K 31/423* (2006.01)
*C07D 277/68* (2006.01)
*C07D 263/58* (2006.01)

(52) U.S. Cl. ............... 514/375; 514/367; 548/169; 548/221

(58) Field of Classification Search ............... 514/367, 514/375; 548/169, 221
See application file for complete search history.

(56) References Cited

U.S. PATENT DOCUMENTS 6,919,362 B1 * 7/2005 Lesieur et al. ............... 514/375

* cited by examiner

*Primary Examiner*—Kamal A. Saeed
*Assistant Examiner*—Joseph R. Kosack
(74) *Attorney, Agent, or Firm*—Hueschen and Sage

(57) ABSTRACT

Compounds of formula (I):

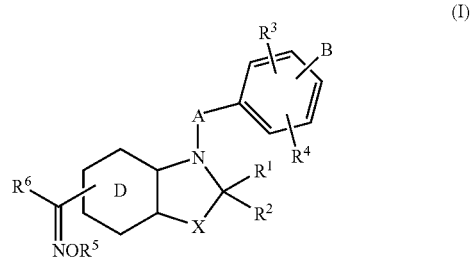

wherein:
X represents oxygen or sulphur or a group $CH_2$ or $$\begin{array}{c} CH, \\ | \\ R^2 \end{array}$$

$R^1$, $R^2$, $R^3$, $R^4$, $R^5$ and $R^6$ are as defined in the description,
A represents an alkylene chain as defined in the description,
B represents alkyl or alkenyl substituted by a group

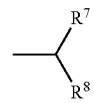

or $R^9$, or B represents a group

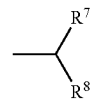

or $R^9$,
D represents a benzene, pyridine, pyrazine, pyrimidine or pyridazine nucleus.

Medicaments

20 Claims, No Drawings

HETEROCYCLIC OXIME COMPOUNDS

FIELD OF THE INVENTION

The present invention relates to new heterocyclic oxime compounds.

The compounds described in the present invention are new and have pharmacological properties that are of special interest: they are excellent hypoglycaemic and hypo-lipidaemic agents.

BACKGROUND OF THE INVENTION

The treatment of non-insulin dependent type II diabetes remains unsatisfactory despite the introduction onto the market of a large number of oral hypoglycaemic compounds designed to facilitate the secretion of insulin and to promote its action in peripheral target tissues.

During the last ten years, a class of compounds having a thiazolidinedione structure (U.S. Pat. No. 5,089,514, U.S. Pat. No. 5,306,726) has demonstrated a marked anti-diabetic activity by promoting sensitivity to insulin in the target peripheral tissues (skeletal muscle, liver, adipose tissue) of animal models having non-insulin dependent type II diabetes. Those compounds also lower the levels of insulin and levels of lipids in the same animal models and induce in vitro differentiation of preadipocyte cell lines into adipocyte cell lines (A. Hiragun et al., J. Cell. Physiol., 1988, 134, 124–130; R. F. Kleitzen et al., Mol. Pharmacol., 1992, 41, 393–398).

The treatment of preadipocyte cell lines with the thiazolidinedione rosiglitazone brings about induction of the expression of specific genes of the lipid metabolism, such as aP2 and adipsin, and also the expression of the glucose transporters GLUT1 and GLUT4, suggesting that the effect of the thiazolidinediones observed in vivo may be mediated via adipose tissue. That specific effect is obtained by the stimulation of nuclear transcription factors: <<peroxisome proliferator-activated receptor gamma>> (PPAR γ2). Such compounds are capable of restoring sensitivity to insulin in peripheral tissues, such as adipose tissue or skeletal muscle (J. E. Gerich, New Engl. Med., 19, 321, 1231–1245).

Compounds having a thiazolidinedione structure (troglitazone, rosiglitazone) have demonstrated disturbing side effects in man, however, including liver problems (Script No. 2470, 1999, Sep. 8th, 25).

A large number of hypoglycaemics have significant side effects (hepatic, cardiac, haematopoietic), which limit their long-term use in the treatment of non-insulin dependent type II diabetes.

The development of new therapeutic agents that are less toxic and that are active over the long term is absolutely necessary in this pathology.

Moreover, hyperlipidaemia is often observed in diabetics (Diabetes Care, 1995, 18 (supplement 1), 86/8/93). The association of hyperglycaemia and hyperlipidaemia increases the risk of cardiovascular disease in diabetics. Hyperglycaemia, hyperlipidaemia and obesity have become pathologies of the modern world marked by the intake of food in large quantities and a chronic lack of exercise.

The increase in frequency of those pathologies calls for the development of new therapeutic agents that are active in such disorders: compounds having an excellent hypoglycaemic and hypolipidaemic activity whilst avoiding the side effects observed with thiazolidinediones are consequently very beneficial in the treatment and/or prophylaxis of those pathologies, and are indicated especially in the treatment of non-insulin dependent type II diabetes for reducing peripheral insulin resistance and for normalising glucose control.

In addition to the fact that they are new, the compounds of the present invention meet the above pharmacological criteria and are excellent hypoglycaemic and hypolipidaemic agents.

DETAILED DESCRIPTION OF THE INVENTION

The present invention relates more especially to compounds of formula (I):

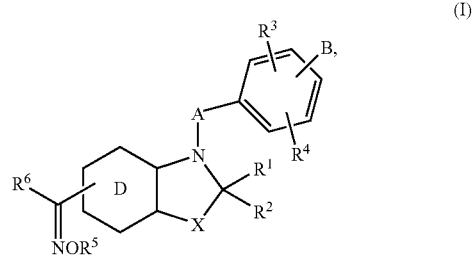

wherein:

X represents an oxygen or sulphur atom, or a group $CH_2$ or

(wherein $R'^2$ together with $R^2$ forms an additional bond), $R^1$ and $R^2$, which may be the same or different, each represent a hydrogen atom, a linear or branched ($C_1$–$C_6$) alkyl group, an aryl group, an aryl-($C_1$–$C_6$)alkyl group in which the alkyl moiety is linear or branched, an aryloxy group, an aryl-($C_1$–$C_6$)alkyloxy group in which the alkyl moiety is linear or branched, a linear or branched ($C_1$–$C_6$) alkoxy group, a hydroxy group, an amino group, a linear or branched ($C_1$–$C_6$)alkylamino group or a di-($C_1$–$C_6$) alkylamino group in which the alkyl moieties are linear or branched, or $R^1$ and $R^2$ together form an oxo, thioxo or imino group, it also being possible for $R^2$ together with $R'^2$ to form an additional bond, A represents a ($C_1$–$C_6$)alkylene chain in which one $CH_2$ group may be replaced by a hetero atom selected from oxygen and sulphur or by a group $NR_a$ (wherein $R_a$ represents a hydrogen atom or a linear or branched ($C_1$–$C_6$)alkyl group), or by a phenylene or naphthylene group, $R^3$ and $R^4$, which may be the same or different, each represent a hydrogen or halogen atom or a group R, OR or NRR' (wherein R and R', which may be the same or different, each represent a hydrogen atom or a linear or branched ($C_1$–$C_6$)alkyl group, a linear or branched ($C_2$–$C_6$)alkenyl group, a linear or branched ($C_2$–$C_6$)alkynyl group, an aryl group, an aryl-($C_1$–$C_6$)alkyl group in which the alkyl moiety is linear or branched, an aryl-($C_2$–$C_6$)alkenyl group in which the alkenyl moiety is linear or branched, an aryl-($C_2$–$C_6$)alkynyl group in which the alkynyl moiety is linear or branched, a heteroaryl group, a heteroaryl-($C_1$–$C_6$)alkyl group in which the alkyl moiety is linear or branched, a heteroaryl-$(C_2$–$C_6)$alkenyl group in which the alkenyl moiety is linear or branched, a heteroaryl-$(C_2$–$C_6)$alkynyl group in which the alkynyl moiety is linear or branched, a $(C_3$–$C_8)$ cycloalkyl group, a $(C_3$–$C_8)$cycloalkyl-$(C_1$–$C_6)$alkyl group in which the alkyl moiety is linear or branched, or a linear or branched $(C_1$–$C_6)$polyhaloalkyl group), or $R^3$ and $R^4$, together with the carbon atoms carrying them, when they are carried by two adjacent carbon atoms, form a ring that has 5 or 6 ring members and that may contain a hetero atom selected from oxygen, sulphur and nitrogen, $R^5$ and $R^6$, which may be the same or different, each can have the same meanings as R as defined hereinbefore, D represents:

a benzene nucleus, in which case X cannot represent a group

as defined hereinbefore, or D represents a pyridine, pyrazine, pyrimidine or pyridazine nucleus, B represents a linear or branched $(C_1$–$C_6)$alkyl group or a linear or branched $(C_2$–$C_6)$-alkenyl group, those groups being substituted:

by a group of formula (II):

wherein: —$R^7$ represents a group

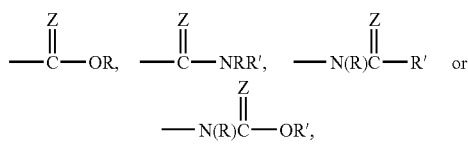

wherein Z represents an oxygen or sulphur atom, and R and R', which may be the same or different are as defined hereinbefore, and $R^8$ represents an aryl group, an arylalkyl group wherein the alkyl moiety contains from 1 to 6 carbon atoms and may be linear or branched, a heteroaryl group, a heteroarylalkyl group wherein the alkyl moiety contains from 1 to 6 carbon atoms and may be linear or branched, CN, tetrazole, —OR, —NRR',

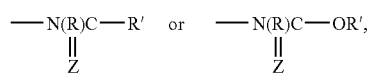

wherein Z is as defined hereinbefore and R and R' which may be the same or different are as defined hereinbefore, or by a group $R^9$, wherein $R^9$ represents a CN, tetrazole,

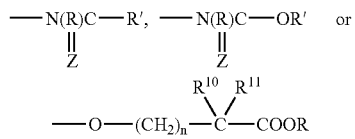

group, wherein Z is as defined hereinbefore and R and R' which may be the same or different are as defined hereinbefore, n represents 0, 1, 2, 3, 4, 5 or 6, and $R^{10}$ and $R^{11}$, which may be the same or different, each represent a hydrogen atom or a linear or branched $(C_1$–$C_6)$alkyl group, it being understood that $R^{10}$ and $R^{11}$ cannot simultaneously represent a hydrogen atom, or B represents a group of formula (II) or a group $R^9$ as defined hereinbefore, it being understood that:

the oxime $R^6$—C(=N—$OR^5$)— can be of Z or E configuration, aryl means a phenyl, naphthyl or biphenyl group, it being possible for those groups to be partially hydrogenated, heteroaryl means any mono- or bi-cyclic aromatic group containing 5 to 10 members, which may be partially hydrogenated in one of the rings in the case of bicyclic heteroaryls and which contains 1 to 3 hetero atoms selected from oxygen, nitrogen and sulphur, it being possible for the aryl and heteroaryl groups thereby defined to be substituted by from 1 to 3 groups selected from linear or branched $(C_1$–$C_6)$alkyl, linear or branched $(C_1$–$C_6)$ polyhaloalkyl, linear or branched $(C_1$–$C_6)$alkoxy, hydroxy, carboxy, formyl, $NR_bR_c$ (wherein $R_b$ and $R_c$, which may be the same or different, each represent a hydrogen atom, a linear or branched $(C_1$–$C_6)$alkyl group, an aryl group or a heteroaryl group), ester, amido, nitro, cyano, and halogen atoms, to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

Among the pharmaceutically acceptable bases there may be mentioned, without implying any limitation, sodium hydroxide, potassium hydroxide, triethylamine, tert-butylamine etc.

Preferred compounds of the invention are compounds of formula (I) wherein $R^1$ and $R^2$ together form an oxo group.

Preference is given to the $R^3$ and $R^4$ groups being hydrogen atoms.

A preferably represents an alkylene chain wherein one $CH_2$ may be replaced by a hetero atom, more especially by an oxygen atom.

The invention relates more especially to compounds of formula (I) wherein A represents an ethyleneoxy group.

Preferred groups D are a benzene nucleus and a pyridine nucleus, more especially a benzene nucleus.

X preferably represents an oxygen atom or sulphur atom, more especially a sulphur atom.

Preferred $R^5$ groups are a hydrogen atom and an alkyl group, for example a methyl group.

$R^6$ advantageously represents a phenyl group which is unsubstituted or substituted by groups such as alkyl, alkoxy and halogen atoms.

Preferred B groups are alkyl or alkenyl groups, more especially alkyl groups substituted by a group

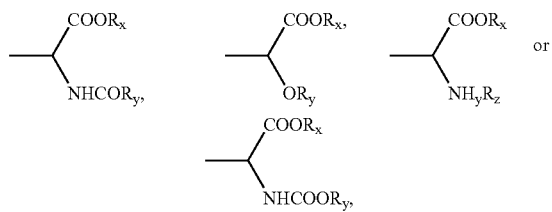

wherein $R_x$, $R_y$ and $R_z$, which may be the same or different, each represent: a hydrogen atom or an alkyl group, for example the groups methyl, ethyl, propyl, isopropyl, butyl, isobutyl, tert-butyl, pentyl, isopentyl, neopentyl or hexyl, a polyhaloalkyl group, for example the groups trifluoromethyl or trifluoroethyl, or a phenyl or benzyl group.

The invention relates more especially to compounds of formula (I) wherein B represents an alkyl or alkenyl group substituted by a group

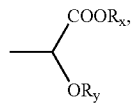

wherein $R_x$ and $R_y$ are as defined hereinbefore.

B also advantageously represents a group

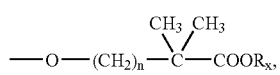

wherein n and $R_x$ are as defined hereinbefore.

The invention relates very advantageously to compounds of formula (I) wherein:

X represents a sulphur atom, $R^1$ and $R^2$ together form an oxo group,

A represents a chain —$CH_2$—$CH_2$—O $R^3$ and $R^4$ simultaneously represent a hydrogen atom, $R^5$ represents a hydrogen atom or an alkyl group, $R^6$ represents a phenyl or substituted phenyl group, more especially substituted by a halogen atom, D represents a benzene nucleus, COORS B represents a group

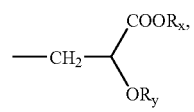

wherein $R_x$ and $R_y$ are as defined hereinbefore.

Even more especially, the invention relates to compounds of formula (I) which are:

methyl 2-ethoxy-3-{4-[2-(6-[(E)-(methoxyimino)(phenyl)methyl]-2-oxo-1,3-benzothiazol-3(2H)-yl)ethoxy]phenyl}propanoate, methyl 2-ethoxy-3-{4-[2-(6-[(Z)-(hydroxyimino)(phenyl)methyl]-2-oxo-1,3-benzothiazol-3 (2H)-yl)ethoxy]phenyl}propanoate, methyl 3-{4-[2-(6-[(methoxyimino)(phenyl)methyl]-2-oxo-1,3-benzothiazol-3(2H)-yl)ethoxy]phenyl}-2-(2,2,2-trifluoroethoxy)propanoate, methyl 3-{4-[2-(6-[(hydroxyimino)(phenyl)methyl]-2-oxo-1,3-benzothiazol-3(2H)-yl)ethoxy]phenyl}-2-(2,2,2-trifluoroethoxy)propanoate, 2-ethoxy-3-{4-[2-(6-[(methoxyimino)(phenyl)methyl]-2-oxo-1,3-benzothiazol-3(2H)-yl)ethoxy]phenyl}propanoic acid, 2-ethoxy-3-{4-[2-(6-[(E)-(methoxyimino)(phenyl)methyl]-2-oxo-1,3-benzothiazol-3(2H)-yl)ethoxy] phenyl}propanoic acid, 2-ethoxy-3-{4-[2-(6-[(E)-(methoxyimino)(phenyl)methyl]-2-oxo-1,3-benzothiazol-3(2H)-yl)ethoxy] phenyl}propanoic acid, enantiomer 1, 2-ethoxy-3-{4-[2-(6-[(E)-methoxyimino)(phenyl)methyl]-2-oxo-1,3-benzothiazol-3(2H)-yl)ethoxy] phenyl}propanoic acid, enantiomer 2, 2-ethoxy-3-{4-[2-(6-[(Z)-(methoxyimino)(phenyl)methyl]-2-oxo-1,3-benzothiazol-3(2H)-yl)ethoxy] phenyl}propanoic acid, 2-ethoxy-3-{4-[2-(6-[(Z)-(methoxyimino)(phenyl)methyl]-2-oxo-1,3-benzothiazol-3(2H)-yl)ethoxy]phenyl} propanoic acid, enantiomer 1, 2-ethoxy-3-{4-[2-(6-[(Z)-(methoxyimino)(phenyl)methyl]-2-oxo-1,3-benzothiazol-3(2H)-yl)ethoxy] phenyl}propanoic acid, enantiomer 2, 2-ethoxy-3-{4-[2-(6-[(hydroxyimino)(phenyl)methyl]-2-oxo-1,3-benzothiazol-3(2H)-yl)ethoxy]phenyl}propanoic acid, 2-ethoxy-3-{4-[2-(6-[(E)(hydroxyimino)(phenyl)methyl]-2-oxo-1,3-benzothiazol-3(2H)-yl)ethoxy]phenyl}propanoic acid, 2-ethoxy-3-{4-[2-(6-[(Z)(hydroxyimino)(phenyl)methyl]-2-oxo-1,3-benzothiazol-3(2H)-yl)ethoxy]phenyl} propanoic acid, methyl 3-{4-[2-(6-[(Z)-(3-chlorophenyl)(methoxyimino)methyl]-2-oxo-1,3-benzothiazol-3(2H)-yl)ethoxy]phenyl}-2-ethoxypropanoate, methyl 3-{4-[2-(6-[(3-chlorophenyl)(hydroxyimino)methyl]-2-oxo-1,3-benzothiazol-3(2H)-yl)ethoxy]phenyl}-2-ethoxypropanoate, methyl 2-methoxy-3-{4-[2-(6-[(methoxyimino)(phenyl)methyl]-2-oxo-1,3-benzothiazol-3(2H)-yl)ethoxy] phenyl}propanoate, 3-{4-[2-(6-[(Z)-(3-chlorophenyl)(methoxyimino)methyl]-2-oxo-1,3-benzothiazol-3(2H)-yl)ethoxy]phenyl}-2-ethoxypropanoic acid, 3-{4-[2-(6-[(methoxyimino)(phenyl)methyl]-2-oxo-1,3-benzothiazol-3(2H)-yl)ethoxy]phenyl}-2-(2,2,2-trifluoroethoxy)propanoic acid, 3-{4-[2-(6-[(E)-(methoxyimino)(phenyl)methyl]-2-oxo-1,3-benzothiazol-3(2H)-yl)ethoxy]phenyl}-2-(2,2,2-trifluoroethoxy)propanoic acid, 3-{4-[2-(6-[(E)-(methoxyimino)(phenyl)methyl]-2-oxo-1,3-benzothiazol-3(2H)-yl)ethoxy]phenyl}-2-(2,2,2-trifluoroethoxy)propanoic acid, enantiomer 1, 3-{4-[2-(6-[(E)-(methoxyimino)(phenyl)methyl]-2-oxo-1,3-benzothiazol-3(2H)-yl)ethoxy]phenyl}-2-(2,2,2-trifluoroethoxy)propanoic acid, enantiomer 2,
3-{4-[2-(6-[(Z)-(methoxyimino)(phenyl)methyl]-2-oxo-1,3-benzothiazol-3(2H)-yl)ethoxy]phenyl}-2-(2,2,2-trifluoroethoxy)propanoic acid,
3-{4-[2-(6-[(Z)-(methoxyimino)(phenyl)methyl]-2-oxo-1,3-benzothiazol-3(2H)-yl)ethoxy]phenyl}-2-(2,2,2-trifluoroethoxy)propanoic acid, enantiomer 1,
3-{4-[2-(6-[(Z)-(methoxyimino)(phenyl)methyl]-2-oxo-1,3-benzothiazol-3(2H)-yl)ethoxy]phenyl}-2-(2,2,2-trifluoroethoxy)propanoic acid, enantiomer 2,
3-{4-[2-(6-[(tert-butoxyimino)(phenyl)methyl]-2-oxo-1,3-benzothiazol-3(2H)-yl)ethoxy]phenyl}-2-ethoxypropanoic acid,
methyl 2-[(tert-butoxycarbonyl)amino]-3-{4-[2-(6-[(methoxyimino)(phenyl)methyl]-2-oxo-1,3-benzothiazol-3(2H)-yl)ethoxy]phenyl}propanoate,
methyl 2-[(tert-butoxycarbonyl)amino]-3-{4-[2-(6-[(hydroxyimino)(phenyl)methyl]-2-oxo-1,3-benzothiazol-3(2H)-yl)ethoxy]phenyl}propanoate,
methyl 2-[(butoxycarbonyl)amino]-3-{4-[2-(6-[(methoxyimino)(phenyl)methyl]-2-oxo-1,3-benzothiazol-3(2H)-yl)ethoxy]phenyl}propanoate,
methyl 3-{4-[2-(6-[(methoxyimino)(phenyl)methyl]-2-oxo-1,3-benzothiazol-3(2H)-yl)ethoxy]phenyl}-2-[(phenoxycarbonyl)amino]propanoate,
methyl 2-{[(benzyloxy)carbonyl]amino}-3-{4-[2-(6-[(hydroxyimino)(phenyl)methyl]-2-oxo-1,3-benzothiazol-3(2H)-yl)ethoxy]phenyl}propanoate,
methyl 2-[(tert-butoxycarbonyl)(methyl)amino]-3-{4-[2-(6-[(methoxyimino)(phenyl)-methyl]-2-oxo-1,3-benzothiazol-3(2H)-yl)ethoxy]phenyl}propanoate,
N-(tert-butoxycarbonyl)-4-[2-(6-[(hydroxyimino)(phenyl)methyl]-2-oxo-1,3-benzothiazol-3 (2H)-yl)ethoxy]phenylalanine,
N-(tert-butoxycarbonyl)-4-[2-(6-[(methoxyimino)(phenyl)methyl]-2-oxo-1,3-benzothiazol-3(2H)-yl)ethoxy]phenylalanine,
methyl 2-amino-3-{4-[2-(6-[(methoxyimino)(phenyl)methyl]-2-oxo-1,3-benzothiazol-3(2H)-yl)ethoxy]phenyl}propanoate,
methyl 2-amino-3-{4-[2-(6-[(hydroxyimino)(phenyl)methyl]-2-oxo-1,3-benzothiazol-3(2H)-yl)ethoxy]phenyl}propanoate,
methyl 3-{4-[2-(6-[(methoxyimino)(phenyl)methyl]-2-oxo-1,3-benzothiazol-3(2H)-yl)ethoxy]phenyl}-2-(methylamino)propanoate.

The enantiomers, diastereoisomers and addition salts with a pharmaceutically acceptable acid or base of the preferred compounds of the invention form an integral part of the invention.

The present invention relates also to a process for the preparation of compounds of formula (I), which process is characterised in that there is used as starting material a compound of formula (III):

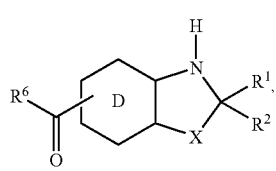

(III)

wherein D, $R^1$, $R^2$, $R^6$ and X are as defined for formula (I), with which there is condensed, in a basic medium, a compound of formula (IV):

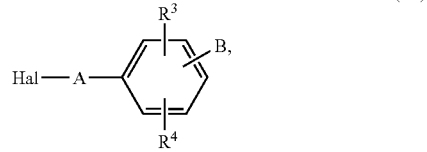

(IV)

wherein A, B, $R^3$ and $R^4$ are as defined for formula (I) and Hal represents a halogen atom, to yield the compound of formula (V):

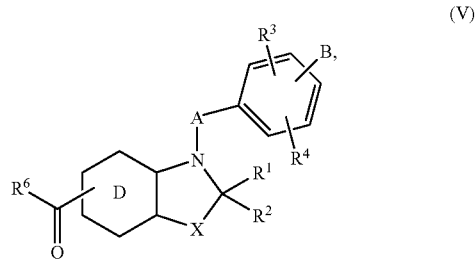

(V)

wherein $R^1$, $R^2$, $R^3$, $R^4$, $R^6$, A, B, D and X are as defined for formula (I), which is subjected to the action of a compound of formula $R^5O$—$NH_2$, wherein $R^5$ is as defined for formula (I), to yield the compound of formula (I):

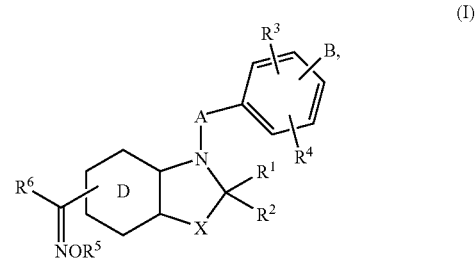

(I)

which may be purified according to a conventional separation technique, which is converted, if desired, into its addition salts with a pharmaceutically acceptable acid or base and which is separated, where applicable, into its isomers according to a conventional separation technique.

An advantageous variant relates to a process for the preparation of compounds of formula (I), characterised in that there is used as starting material a compound of formula (III):

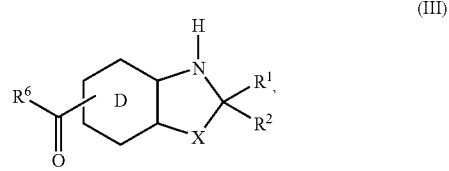

(III)

wherein D, $R^1$, $R^2$, $R^6$ and X are as defined for formula (I), with which there is condensed a compound of formula R⁵O—NH₂, wherein R⁵ is as defined for formula (I), to yield the compound of formula (VI):

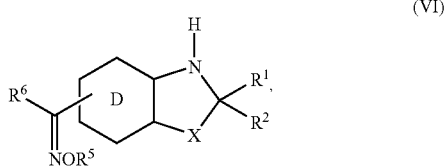

(VI)

wherein R¹, R², R⁵, R⁶, D and X are as defined for formula (I), with which there is condensed, in a basic medium, a compound of formula (IV):

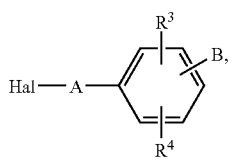

(IV)

wherein A, B, R³ and R⁴ are as defined for formula (I) and Hal represents a halogen atom, to yield the compound of formula (I):

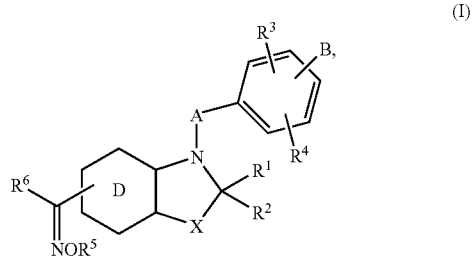

(I)

which may be purified according to a conventional separation technique, which is converted, if desired, into its addition salts with a pharmaceutically acceptable acid or base and which is separated, where applicable, into its isomers according to a conventional separation technique.

The compounds of formula (III) are commercially available or readily accessible to the person skilled in the art by means of chemical reactions which are customary or described in the literature.

Another aspect of the invention relates also to compounds of formula (V):

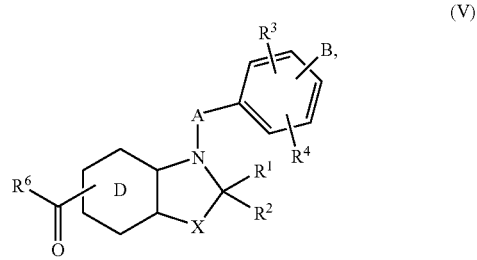

(V)

wherein R⁶, D, X, A, R¹, R², R³, R⁴ and B are as defined for compounds of formula (I), for use as intermediates for the synthesis of compounds of formula I and as hypoglycaemic and hypolipidaemic agents.

The compounds of the present invention have very valuable pharmacological properties.

The compounds demonstrate especially an excellent activity in lowering blood glucose levels. As a result of such properties they can be used therapeutically in the treatment and/or prophylaxis of hyperglycaemia, dyslipidaemia and, more especially, in the treatment of non-insulin dependent type II diabetes, glucose intolerance, disorders associated with syndrome X (including hypertension, obesity, insulin resistance, atherosclerosis, hyperlipidaemia), coronary artery disease and other cardiovascular diseases (including arterial hypertension, heart failure, venous insufficiency), renal disorders (including glomerulonephritis, glomerulosclerosis, nephrotic syndrome, hypertensive nephrosclerosis), retinopathy, disorders associated with the activation of endothelial cells, psoriasis, polycystic ovary syndrome, dementia, complications of diabetes, and osteoporosis.

They can be used as aldose reductase inhibitors for improving cognitive functions in dementia and the complications of diabetes, intestinal inflammatory disorders, myotonic dystrophy, pancreatitis, arteriosclerosis, xanthoma.

The activity of these compounds is also recommended for the treatment and/or prophylaxis of other diseases, including type I diabetes, hypertriglyceridaemia, syndrome X, insulin resistance, dyslipidaemia in diabetics, hyperlipidaemia, hypercholesterolaemia, arterial hypertension, heart failure, and cardiovascular disease, especially atherosclerosis.

The compounds are furthermore indicated for use in the regulation of appetite, especially in the regulation of food intake in subjects suffering from disorders such as obesity, anorexia, bulimia and anorexia nervosa.

The compounds can accordingly be used in the prevention or treatment of hypercholesterolaemia, obesity with advantageous effects on hyperlipidaemia, hyperglycaemia, osteoporosis, glucose intolerance, insulin resistance or disorders in which insulin resistance is a secondary physiopathological mechanism.

The use of those compounds enables reduction of total cholesterol, body weight, leptin resistance, plasma glucose, triglycerides, LDLs, VLDLs and also plasma free fatty acids. The compounds can be used in association with HMG CoA reductase inhibitors, fibrates, nicotinic acid, cholestyramine, colestipol, probucol, GLP1, metformin, biguanides or glucose reabsorption inhibitors and can be administered together or at different times to act in synergy in the patient treated.

They furthermore exhibit activity in cancer pathologies and especially hormone-dependent cancers, such as breast cancer or colon cancer, and also have an inhibiting effect on the angiogenesis processes implicated in such pathologies.

Among the pharmaceutical compositions according to the invention there may be mentioned more especially those that are suitable for oral, parenteral, nasal, per- or trans-cutaneous, rectal, perlingual, ocular or respiratory administration and especially tablets and dragées, sublingual tablets, sachets, paquets, capsules, glossettes, lozenges, suppositories, creams, ointments, dermal gels and drinkable or injectable ampoules.

The useful dosage varies according to the sex, age and weight of the patient, the administration route, the nature of the therapeutic indication and any associated treatments, and ranges from 0.1 mg to 1 g per 24 hours in 1 or more administrations.

The following Examples illustrate the invention and do not limit it in any way.

EXAMPLE 1

Methyl 2-ethoxy-3-{4-[2-(6-[(methoxyimino)(phenyl)methyl]-2-oxo-1,3-benzothiazol-3(2H)-yl)ethoxy]phenyl}propanoate

Step A: Methyl 3-[4-(2-chloroethoxy)phenyl]-2-ethoxy-2-propenoate

To 150 ml of freshly distilled tetrahydrofuran, placed in a bath of ice-cold water at 0° C., under argon, add sodium hydride (0.0473 mol) and then methyl 2-ethoxy-2-diethylphosphonoacetate (0.0394 mol) while maintaining the temperature at 0° C. After stirring for 1 hour, add 4-(2-chloroethoxy)benzaldehyde (0.0394 mol) dissolved in a minimum of freshly distilled tetrahydrofuran, under argon at 0° C. Stir the solution for 1 hour at 0° C. Allow the solution to return to ambient temperature while stirring for 16 hours. Evaporate off the tetrahydrofuran. Add 100 ml of water and then extract with 100 ml of dichloromethane twice. The organic phase is washed with water, dried over MgSO$_4$ and then evaporated. The oily product is purified over a column of silica gel using the eluant mixture: petroleum ether/dichloromethane (1/1). The title compound is obtained in the form of an oil.

Step B: Methyl 3-[4-(2-chloroethoxy)phenyl]-2-ethoxypropanoate

To 100 ml of tetrahydrofuran add the compound obtained in Step A (0.0175 mol) and then palladium-on-carbon (0.2 g). Stir at ambient temperature under hydrogen for 1 day. Filter off the palladium-on-carbon and then evaporate the filtrate. The oily product is purified on a column of silica gel using the eluant mixture: petroleum ether/dichloromethane (1/1). The title compound is obtained in the form of an oil.

Step C: Methyl 3-{4-[2-(6-benzoyl-2-oxo-1,3-benzothiazol-3(2H)-yl)ethoxy]phenyl}-2-ethoxypropanoate To 20 ml of dimethylformamide add potassium carbonate (0.01044 mol) and then 6-benzoylbenzothiazolinone (0.00453 mol). Heat at 100° C. for 1 hour. Add the compound obtained in Step B (0.00348 mol) and heat at 150° C. for 16 hours. Evaporate off the dimethylformamide. Take up the residue in 50 ml of water and then extract with 50 ml of dichloromethane twice. The organic phase is dried over MgSO$_4$ and then evaporated. The residue is recrystallised from methanol and yields the title compound in the form of a solid.
Melting point: 118–119° C.

Step D: Methyl 2-ethoxy-3-{4-[2-(6-[(methoxyimino)(phenyl)methyl]-2-oxo-1,3-benzothiazol-3(2H)-yl)ethoxy]phenyl}propanoate To 30 ml of methanol add the compound obtained in Step C (0.00198 mol), O-methyl-hydroxylamine hydrochloride (0.00594 mol) and pyridine (0.00594 mol). Heat at reflux for 3 hours. Evaporate to dryness. Add 100 ml of hydrochloric acid (1N) and then extract with 50 ml of dichloromethane twice. The organic phase is dried over MgSO$_4$ and then evaporated to yield the title compound.

EXAMPLE 1a

Methyl 2-ethoxy-3-{4-[2-(6[(E)-(methoxyimino)(phenyl)methyl]-2-oxo-1,3-benzothiazol-3(2H)-yl)ethoxy]phenyl}propanoate The compound obtained in Step D of Example 1 is taken up in diethyl ether and the title compound is precipitated in selective manner and filtered off to yield the (E) isomer.
Melting point: 122–123° C.

EXAMPLE 1b

Methyl 2-ethoxy-3-{4-[2-(6-[(Z)-(methoxyimino)(phenyl)methyl]-2-oxo-1,3-benzothiazol-3(2H)-yl)ethoxy]phenyl}propanoate The filtrated obtained in Example 1a is evaporated and the residue obtained is recrystallised to yield the title compound.

EXAMPLE 2

Methyl 2-ethoxy-3-{4-[2-(6 [(Z)-(hydroxyimino)(phenyl)methyl]-2-oxo-1,3-benzothiazol-3(2H)-yl)ethoxy]phenyl}propanoate

Step A: Methyl 3-{4-[2-(6-benzoyl-2-oxo-1,3-benzothiazol-3(2H)-yl)ethoxy]-phenyl}-2-ethoxypropanoate To 20 ml of dimethylformamide add potassium carbonate (0.01044 mol) and then 6-benzoylbenzothiazolinone (0.00453 mol). Heat at 100° C. for 1 hour. Add the compound obtained in Step B of Example 1 (0.00348 mol) and heat at 150° C. for 16 hours. Evaporate off the dimethylformamide. Take up the residue in 50 ml of water and then extract with 50 ml of dichloromethane twice. The organic phase is dried over MgSO$_4$ and then evaporated. The residue is recrystallised form methanol and yields the title compound in the form of a solid.
Melting point: 118–119° C.

Step B: Methyl 2-ethoxy-3-{4-[2-(6-[(Z)-(hydroxyimino)(phenyl)methyl]-2-oxo-1,3-benzothiazol-3(2H)-yl)ethoxy]phenyl}propanoate To 30 ml of methanol add the compound obtained in Step A (0.00198 mol), hydroxylamine hydrochloride (0.00594 mol) and pyridine (0.00594 mol). Heat at reflux for 3 hours. Evaporate to dryness. Add 100 ml of hydrochloric acid (1N) and then extract with 50 ml of dichloromethane twice. The organic phase is dried over MgSO$_4$ and then evaporated. The (E) compound is precipitated using diethyl ether. The filtrate is then evaporated to yield the (Z) compound of the title, which is recrystallised from methanol.
Melting point: 114–115° C.

EXAMPLE 3

Methyl 3-{4-[2-(6-[(methoxyimino)(phenyl)methyl]-2-oxo-1,3-benzothiazol-3(2H)-yl)ethoxy]phenyl}-2-(2,2,2-trifluoroethoxy)-propanoate

Step A: Methyl 3-[4-(2-chloroethoxy)phenyl]-2-(2,2,2-trifluoroethoxy)-2-propenoate The procedure is as in Step A of Example 1, replacing the 2-ethoxy-2-diethylphosphono-acetate by 2-(2,2,2-trifluoromethoxy)-2-diethylphosphonoacetate.
White solid.
Melting point: 50–51° C.

Step B: Methyl 3-[4-(2-chloroethoxy)phenyl]-2-(2, 2,2-trifluoroethoxy)propanoate Starting from the compound obtained in Step A, the procedure is as in Step B of Example 1.
Oil.

Step C: Methyl 3-{4-[2-(6-benzoyl-2-oxo-1,3-benzothiazol-3(2H)-yl)ethoxy]-phenyl}-2-(2,2,2-trifluoroethoxy)propanoate Starting from the compound obtained in Step B, the procedure is as in Step C of Example 1.
Solid.
Melting point: 46–47° C.

Step D: Methyl 3-{4-[2-(6-[(methoxyimino)(phenyl)methyl]-2-oxo-1,3-benzo-thiazol-3(2H)-yl)ethoxy]phenyl}-2-(2,2,2-trifluoroethoxy)propanoate Starting from the compound obtained in Step C, the procedure is as in Step B of Example 2, replacing the hydroxylamine by O-methylhydroxylamine.
Solid.
Melting point: 67–68° C.

EXAMPLE 4

Methyl 3-{4-[2-(6-[(hydroxyimino)(phenyl)methyl]-2-oxo-1,3-benzothiazol-3(2H)-yl)ethoxy]phenyl}-2-(2,2,2-trifluoroethoxy)-propanoate Starting from the compound obtained in Step C of Example 3, the procedure is as in Step B of Example 2.
Solid.
Melting point: 55–56° C.

EXAMPLE 5

2-Ethoxy-3-{4-[2-(6-[(methoxyimino)(phenyl)methyl]-2-oxo-1,3-benzothiazol-3(2H)-yl)ethoxy]phenyl}propanoic acid The title compound is obtained by hydrolysis of the compound obtained in Example 1 using KOH in a methanol/water mixture.

EXAMPLE 5a

2-Ethoxy-3-{4-[2-(6-[(E)-(methoxyimino)(phenyl)methyl]-2-oxo-1,3-benzothiazol-3(2H)-yl)ethoxy]phenyl}propanoic acid The title compound is obtained by hydrolysis of the compound obtained in Example 1a using KOH in a methanol/water mixture.
Solid.
Melting point: 151–152° C.

Starting from the compound obtained in Example 5a, Examples 5a(1) and 5a(2) are obtained by chiral separation on CHIRALPAK AD, using an n-heptane/iso-propanol/trifluoroacetic acid mixture (750/250/1) and detection at 280 nm.

EXAMPLE 5a(1)

2-Ethoxy-3-{4-[2-(6-[(E)-(methoxyimino)(phenyl)methyl]-2-oxo-1,3-benzothiazol-3(2H)-yl)ethoxy]phenyl}propanoic acid, enantiomer 1

The title compound is obtained with an optical purity greater than 99%.

EXAMPLE 5a(2)

2-Ethoxy-3-{4-[2-(6-[(E)-(methoxyimino)(phenyl)methyl]-2-oxo-1,3-benzothiazol-3(2H)-yl)ethoxy]phenyl}propanoic acid, enantiomer 2

The title compound is obtained with an optical purity of 98.6%.

EXAMPLE 5b

2-Ethoxy-3-{4-[2-(6-[(Z)-(methoxyimino)(phenyl)methyl]-2-oxo-1,3-benzothiazol-3(2H)-yl)ethoxy]phenyl}propanoic acid The title compound is obtained by hydrolysis of the compound obtained in Example 1b, using KOH in a methanol/water mixture.

Starting from the compound obtained in Example 5b, Examples 5b(1) and 5b(2) are obtained by means of chiral chromatographic separation.

EXAMPLE 5b(1)

2-Ethoxy-3-{4-[2-(6-[(Z)-(methoxyimino)(phenyl)methyl]-2-oxo-1,3-benzothiazol-3(2H)-yl)ethoxy]phenyl}propanoic acid, enantiomer 1

EXAMPLE 5b(2)

2-Ethoxy-3-{4-[2-(6-[(Z)-(methoxyimino)(phenyl)methyl]-2-oxo-1,3-benzothiazol-3(2H)-yl)ethoxy]phenyl}propanoic acid, enantiomer 2

EXAMPLE 6

2-Ethoxy-3-{4-[2-(6-[(hydroxyimino)(phenyl)methyl]-2-oxo-1,3-benzothiazol-3(2H)-yl)ethoxy]phenyl}propanoic acid Starting from the (Z, E) mixture obtained in Example 2, the procedure is as in Example 5.
Melting point: 84–85° C.

EXAMPLE 6a

2-Ethoxy-3-{4-[2-(6-[(E)(hydroxyimino)(phenyl)methyl]-2-oxo-1,3-benzothiazol-3(2H)-yl)ethoxy]phenyl}propanoic acid Starting from the (E) compound obtained in Example 2, the procedure is as in Example 5.

EXAMPLE 6b

2-Ethoxy-3-{4-[2-(6-[(Z)(hydroxyimino)(phenyl)methyl]-2-oxo-1,3-benzothiazol-3(2H)-yl)ethoxy]phenyl}propanoic acid Starting from the (Z) compound obtained in Example 2, the procedure is as in Example 5.

EXAMPLE 7

Methyl 3-{4-[2-(6-[(Z)-(3-chlorophenyl)(methoxyimino)methyl]-2-oxo-1,3-benzothiazol-3(2H)-yl)ethoxy]phenyl}-2-ethoxypropanoate

Step A: Methyl 3-{4-[2-(6-(3-chlorobenzoyl)-2-oxo-1,3-benzothiazol-3(2H)-yl)ethoxy]phenyl}-2-ethoxypropanoate The procedure is as in Step C of Example 1, replacing the 6-benzoylbenzothiazolinone by 6-(3-chloro)benzoylbenzothiazolinone.

Melting point: 100–101° C.

Step B: Methyl 3-{4-[2-(6-[(Z)-(3-chlorophenyl)(methoxyimino)methyl]-2-oxo-1,3-benzothiazol-3(2H)-yl)ethoxy]phenyl}-2-ethoxypropanoate Starting from the compound obtained in Step A, the procedure is as in Step B of Example 2, replacing the hydroxylamine by O-methylhydroxylamine. Solid.

Melting point: 113–114° C.

EXAMPLE 8

Methyl 3-{4-[2-(6-[(3-chlorophenyl)(hydroxyimino)methyl]-2-oxo-1,3-benzothiazol-3(2H)-yl)ethoxy]phenyl}-2-ethoxypropanoate Starting from the compound obtained in Step A of Example 7, the procedure is as in Step B of Example 2. The two (Z) and (E) compounds are not separated.

Solid.
Melting point: 146–147° C.

EXAMPLE 9

Methyl 2-methoxy-3-{4-[2-(6-[(methoxyimino)(phenyl)methyl]-2-oxo-1,3-benzothiazol-3(2H)-yl)ethoxy]phenyl}propanoate The procedure is as in Example 1, replacing the 2-ethoxy-2-diethylphosphonoacetate by 2-methoxy-2-diethylphosphonoacetate.

Melting point: 142–144° C.

EXAMPLE 10

Methyl 2-[(tert-butoxycarbonyl)amino]-3-{4-[2-(6-[(methoxyimino)-(phenyl)methyl]-2-oxo-1,3-benzothiazol-3(2H)-yl)ethoxy]phenyl}-propanoate

Step A: Methyl 2-[(tert-butoxycarbonyl)amino-3-(4-hydroxyphenyl)propanoate 25 g of methyl 2-amino-3-(4-hydroxyphenyl)propionate (128 mmol) are dissolved in 110 ml of methanol. The temperature is lowered to 0° C., and 53.4 ml of triethylamine and then 30.73 g of di-tert-butyl dicarbonate are added in succession. The mixture is allowed to return to ambient temperature and the reaction mixture is stirred overnight.

The solvent is evaporated off and the residue is purified by column chromatography on silica gel (eluant: cyclohexane/ethyl acetate 7/3) in order to obtain the title compound in the form of a white solid.

Melting point: 106–108° C.

Step B: Methyl 2-[(tert-butoxycarbonyl)amino]-3-[4-(2-chloroethoxy)phenyl]-propanoate 5 g (16.94 mmol) of the compound obtained in Step A are dissolved in 100 ml of acetone, and 7.02 g of potassium carbonate are added. The mixture is heated at reflux of the solvent and stirred for 1 hour; then 24.29 g of 1-bromo-2-chloroethane are added and the reaction mixture is stirred at reflux for 12 days.

The mixture is filtered and the filtrate is evaporated. The residue obtained is purified by column chromatography on silica gel (eluant:petroleum ether/AcOEt 8/2) to yield the title compound in the form of a white solid.

Melting point: 52–54° C.

Step C: Methyl 3-{4-[2-(6-benzoyl-2-oxo-1,3-benzothiazol-3(2H)-yl)ethoxy]phenyl}-2-[(tert-butoxycarbonyl)amino]propanoate 3.6 g of 6-benzoylthiazolinone are dissolved in 40 ml of dimethylformamide, and then 4.87 g of potassium carbonate are added and the temperature is brought to 80° C. for 1 hour. 6.05 g of the compound obtained in Step B are then added and the reaction mixture is stirred at 100° C. overnight.

The mixture is filtered and the solvent is evaporated to dryness. The residue is taken up in ethyl acetate and washed with saturated sodium hydrogen carbonate solution. The combined organic phases are dried over magnesium sulphate and concentrated. The second residue is purified by column chromatography on silica gel (eluant: petroleum ether/AcOEt 6/4). The title compound is obtained in the form of a yellow solid.

Melting point: 76–79° C.

Step D: Methyl 2-[(tert-butoxycarbonyl)amino]-3-{4-[2-(6-[(methoxyimino)-(phenyl)methyl]-2-oxo-1,3-benzothiazol-3(2H)-yl)ethoxy]phenyl}-propanoate Starting from the compound obtained in Step C, the procedure is as in Step B of Example 2, replacing the hydroxylamine by O-methylhydroxylamine.

Oil.

EXAMPLE 11

Methyl 2-[(tert-butoxycarbonyl)amino]-3-{4-[2-(6[(hydroxyimino)-(phenyl)methyl]-2-oxo-1,3-benzothiazol-3(2H)-yl)ethoxy]phenyl}-propanoate Starting from the compound obtained in Step C of Example 10, the procedure is as in Step B of Example 2. The two (Z) and (E) compounds are not separated.

Melting point: 80–82° C.

EXAMPLE 12

Methyl 2-[(butoxycarbonyl)amino]-3-{4-[2-(6-[(methoxyimino)-(phenyl)methyl]-2-oxo-1,3-benzothiazol-3(2H)-yl)ethoxy]phenyl}-propanoate

Step A: Methyl 2-amino-3-{4-[2-(6-benzoyl-2-oxo-1,3-benzothiazol-3(2H)-yl)-ethoxy]phenyl}propanoate trifluoroacetate 4 g of the compound obtained in Step C of Example 10 are dissolved in 200 ml of dichloromethane and the temperature is lowered to 0° C. 12.47 ml of trifluoroacetic acid are then added and the reaction mixture is stirred at ambient temperature for 4 hours.

The solvent is evaporated off, the mixture is taken up in water and the pH is adjusted to 7–8. The aqueous phase is extracted with dichloromethane; the organic phases are then dried (MgSO$_4$) and evaporated. The residue is triturated in diethyl ether and filtered under suction to yield the title compound in the form of a white solid.

Melting point: 130–132° C.

Step B: Methyl 3-{4-[2-(6-benzoyl-2-oxo-1,3-benzothiazol-3(2H)-yl)ethoxy]phenyl}-2-[(butoxycarbonyl)amino]propanoate 700 mg of the compound obtained in Step A are dissolved in 10 ml of ethyl acetate; 0.494 ml of triethylamine is then added and the temperature is lowered to 0° C. 0.229 ml of butyl chloroformate is added and the mixture is allowed to return to ambient temperature and is stirred overnight.

The reaction mixture is filtered and the filtrate is concentrated. The residue is purified by column chromatography on silica gel (eluant: petroleum ether/AcOEt 7/3). The title compound is obtained in the form of a white solid.

Melting point: 74–76° C.

Step C: Methyl 2-[(butoxycarbonyl)amino]-3-{4-[2-(6-[(methoxyimino)-(phenyl)methyl]-2-oxo-1,3-benzothiazol-3(2H)-yl)ethoxy]phenyl)}-propanoate Starting from the compound obtained in Step B, the procedure is as in Step B of Example 2, replacing the hydroxylamine by O-methylhydroxylamine.

EXAMPLE 13

Methyl 3-{4-[2-(6-[(methoxyimino)(phenyl)methyl]-2-oxo-1,3-benzothiazol-3(2H)-yl)ethoxy]phenyl}-2-[(phenoxycarbonyl)amino]-propanoate

Step A: Methyl 3-{4-[2-(6-benzoyl-2-oxo-1,3-benzothiazol-3(2H)-yl)ethoxy]phenyl}-2-[(phenoxycarbonyl)amino]propanoate 1.5 g of the compound obtained in Step A of Example 12 are dissolved in 20 ml of ethyl acetate; 1.06 ml of triethylamine are then added and the temperature is lowered to 0° C. 0.637 ml of phenyl chloroformate is then added and the mixture is allowed to return to ambient temperature and is stirred overnight.

The reaction mixture is filtered and the filtrate is concentrated. The residue is purified by column chromatography on silica gel (eluant: petroleum ether/AcOEt 6/4). The title compound is obtained in the form of a white solid.

Melting point: 74–76° C.

Step B: Methyl 3-{4-[2-(6-[(methoxyimino)(phenyl)methyl]-2-oxo-1,3-benzothiazol-3(2H)-yl)ethoxy]phenyl}-2-[(phenoxycarbonyl)amino]propanoate Starting from the compound obtained in Step A, the procedure is as in Step B of Example 2, replacing the hydroxylamine by O-methylhydroxylamine.

EXAMPLE 14

Methyl 2-{[(benzyloxy)carbonyl]amino}-3-{4-[2-(6[(hydroxyimino)-(phenyl)methyl]-2-oxo-1,3-benzothiazol-3(2H)-yl)ethoxy]phenyl}-propanoate

Step A: Methyl 3-{4-[2-(6-benzoyl-2-oxo-1,3-benzothiazol-3(2H)-yl)ethoxy]phenyl}-2-{[(benzyloxy)carbonyl]amino}propanoate 1.5 g of the compound obtained in Step A of Example 12 are dissolved in 20 ml of ethyl acetate; 1.06 ml of triethylamine are then added and the temperature is lowered to 0° C. 0.725 ml of benzyl chloroformate are added and the mixture is allowed to return to ambient temperature and is stirred overnight.

The reaction mixture is filtered and the filtrate is concentrated. The residue is purified by column chromatography on silica gel (eluant: petroleum ether/AcOEt 6/4). The title compound is obtained in the form of a white solid.

Melting point: 64–68° C.

Step B: Methyl 2-{[(benzyloxy)carbonyl]amino}-3-{4-[2-(6-[(hydroxyimino)-(phenyl)methyl]-2-oxo-1,3-benzothiazol-3(2H)-yl)ethoxy]phenyl}-propanoate Starting from the compound obtained in Step A, the procedure is as in Step B of Example 2.

EXAMPLE 15

Methyl 2-(acetylamino)-3-{4-[2-(6-[(methoxyimino)(phenyl)methyl]-2-oxo-1,3-benzothiazol-3(2H)-yl)ethoxy]phenyl}propanoate

Step A: Methyl 2-(acetylamino)-3-{4-[2-(6-benzoyl-2-oxo-1,3-benzothiazol-3(2H)-yl)ethoxy]phenyl}propanoate 500 mg of the compound obtained in Step A of Example 12 are dissolved in 10 ml of ethyl acetate; 0.353 ml of triethylamine is then added and the temperature is lowered to 0° C. 0.121 ml of acetyl chloride is added and the mixture is allowed to return to ambient temperature and is stirred overnight.

The reaction mixture is filtered and the filtrate is concentrated. The residue is recrystallised from a toluene/isopropanol (95/5) mixture. The title compound is obtained in the form of a white solid.

Melting point: 142–144° C.

Step B: Methyl 2-(acetylamino)-3-{4-[2-(6-[(methoxyimino)(phenyl)methyl]-2-oxo-1,3-benzothiazol-3(2H)-yl)ethoxy]phenyl}propanoate Starting from the compound obtained in Step A, the procedure is as in Step B of Example 2, replacing the hydroxylamine by O-methylhydroxylamine.

EXAMPLE 16

Methyl 2-(butyrylamino)-3-{4-[2-(6-[(hydroxyimino)(phenyl)methyl]-2-oxo-1,3-benzothiazol-3(2H)-yl)ethoxy]phenyl}propanoate Step A: Methyl 3-{4-[2-(6-benzoyl-2-oxo-1,3-benzothiazol-3(2H)-yl)ethoxy]phenyl}-2-(butyrylamino)propanoate 500 mg of the compound obtained in Step A of Example 12 are dissolved in 10 ml of ethyl acetate; 0.353 ml of triethylamine is then added and the temperature is lowered to 0° C. 0.177 ml of butyryl chloride is added and the mixture is allowed to return to ambient temperature and is stirred overnight.

The reaction mixture is filtered and the filtrate is concentrated. The residue is purified by column chromatography on silica gel (eluant: petroleum ether/AcOEt 6/4). The title compound is obtained in the form of a white solid.

Melting point: 67–69° C.

Step B: Methyl 2-(butyrylamino)-3-{4-[2-(6-[(hydroxyimino)(phenyl)methyl]-2-oxo-1,3-benzothiazol-3(2H)-yl)ethoxy]phenyl}propanoate Starting from the compound obtained in Step A, the procedure is as in Step B of Example 2.

EXAMPLE 17

Methyl 2-(benzoylamino)-3-{4-[2-(6-[(hydroxyimino)(phenyl)-methyl]-2-oxo-1,3-benzothiazol-3(2H)-yl)ethoxy]phenyl}propanoate Step A: Methyl 2-(benzoylamino)-3-{4-[2-(6-benzoyl-2-oxo-1,3-benzothiazol-3(2H)-yl)ethoxy]phenyl}propanoate 500 mg of the compound obtained in Step A of Example 12 are dissolved in 10 ml of ethyl acetate; 0.353 ml of triethylamine is then added and the temperature is lowered to 0° C. 0.197 ml of benzoyl chloride is added and the mixture is allowed to return to ambient temperature and is stirred overnight.

The reaction mixture is filtered and the filtrate is concentrated. The residue is purified by column chromatography on silica gel (eluant: petroleum ether/AcOEt 7/3). The title compound is obtained in the form of a white solid.

Melting point: 124–126° C.

Step B: Methyl 2-(benzoylamino)-3-{4-[2-(6-[(hydroxyimino)(phenyl)methyl]-2-oxo-1,3-benzothiazol-3(2H)-yl)ethoxy]phenyl}propanoate Starting from the compound obtained in Step A, the procedure is as in Step B of Example 2.

EXAMPLE 18

Methyl 3-{4-[2-(6-[(methoxyimino)(phenyl)methyl]-2-oxo-1,3-benzothiazol-3(2H)-yl)ethoxy]phenyl}-2-[(phenylacetyl)amino]-propanoate Step A: Methyl 3-{4-[2-(6-benzoyl-2-oxo-1,3-benzothiazol-3(2H)-yl)ethoxy]phenyl}-2-[(phenylacetyl)amino]propanoate 500 mg of the compound obtained in Step A of Example 12 are dissolved in 10 ml of ethyl acetate; 0.353 ml of triethylamine is then added and the temperature is lowered to 0° C. 0.226 ml of phenylacetyl chloride is added and the mixture is allowed to return to ambient temperature and is stirred overnight.

The reaction mixture is filtered and the filtrate is concentrated. The residue is purified by column chromatography on silica gel (eluant: petroleum ether/AcOEt 8/2). The title compound is obtained in the form of a white solid.

Melting point: 122–124° C.

Step B: Methyl 3-{4-[2-(6-[(methoxyimino)(phenyl)methyl]-2-oxo-1,3-benzothiazol-3(2H)-yl)ethoxy]phenyl}-2-[(phenylacetyl)amino]propanoate Starting from the compound obtained in Step A, the procedure is as in Step B of Example 2, replacing the hydroxylamine by O-methylhydroxylamine.

EXAMPLE 19

Methyl 2-amino-3-{4-[2-(6-[(methoxyimino)(phenyl)methyl]-2-oxo-1,3-benzothiazol-3(2H)-yl)ethoxy]phenyl}propanoate Dissolve the compound obtained in Example 10 (1 eq.) in 250 ml of anhydrous DCM and add TFA (20 eq.) dropwise. Stir for 5 hours and evaporate. Take up in water and render alkaline using 10% $K_2CO_3$. Extract with ethyl acetate. Wash the organic phases with water, dry over $MgSO_4$, filter and evaporate. Take up in a minimum of methanol and bubble HCl gas through the mixture for 30 minutes. Evaporate to dryness and take up in diisopropyl ether. Filter off the precipitate and recrystallise from diethyl ether.

Melting point: 112–114° C.

EXAMPLE 20

Methyl 2-amino-3-{4-[2-(6-[(hydroxyimino)(phenyl)methyl]-2-oxo-1,3-benzothiazol-3(2H)-yl)ethoxy]phenyl}propanoate Starting from the compound obtained in Example 11, the procedure is as in Example 19.

Melting point: 19–122° C.

EXAMPLE 21

Methyl 2-[(tert-butoxycarbonyl)(methyl)amino]-3-{4-[2-(6-[(methoxyimino)(phenyl)methyl]-2-oxo-1,3-benzothiazol-3(2H)-yl)ethoxy]phenyl}propanoate Step A: Methyl 3-{4-[2-(6-benzoyl-2-oxo-1,3-benzothiazol-3(2H)-yl)ethoxy]phenyl}-2-[(tert-butoxycarbonyl)(methyl)amino]propanoate Dissolve the compound obtained in Step C of Example 10 (1 eq.) and $CH_3I$ (2 eq.): in 55 ml of anhydrous DMF and place in an ice bath at 0° C. Add NaH (1.5 eq.) in portions. Allow to return to ambient temperature. Hydrolyse, acidify with 1N HCl and filter. Purify the resulting crude product by chromatography on silica gel (eluant:diethyl ether/toluene 2/8).

Oil.

Step B: Methyl 2-[(tert-butoxycarbonyl)(methyl) amino]-3-{4-[2-(6-[(methoxy-imino)(phenyl)methyl]-2-oxo-1,3-benzothiazol-3(2H)-yl)ethoxy]phenyl}-propanoate Starting from the compound obtained in Step A, the procedure is as in Step B of Example 2, replacing the hydroxylamine by O-methylhydroxylamine.

EXAMPLE 22

Methyl 3-{4-[2-(6-[(methoxyimino)(phenyl)methyl]-2-oxo-1,3-benzothiazol-3(2H)-yl)ethoxy]phenyl}-2-(methylamino)propanoate Starting from the compound obtained in Example 21, the procedure is as in Example 19.

EXAMPLE 23

Methyl 2-(2-hydroxyphenyl)-3-{4-[2-(6-[(methoxyimino)(phenyl)-methyl]-2-oxo-1,3-benzothiazol-3(2H)-yl)ethoxy]phenyl}propanoate 1st method:

Step A: 6-Benzoyl-3-(2-{4-[(2-oxo-2,3-dihydro-1-benzofuran-3-yl)methyl]phenoxy}-ethyl)-1,3-benzothiazol-2(3H)-one Starting from 6-benzoylbenzothiazolinone and 3-[4-(2-chloroethoxy)benzyl]-1-benzofuran-2(3H)-one, the procedure is as in Step C of Example 1.

Step B: 6-[(Methoxyimino)(phenyl)methyl]-3-(2-{4-[(2-oxo-2,3-dihydro-1-benzofuran-3-yl)methyl]phenoxy}ethyl)-1,3-benzothiazol-2(3H)-one Starting from the compound obtained in Step A, the procedure is as in Step B of Example 2, replacing the hydroxylamine by O-methylhydroxylamine.

Step C: Methyl 2-(2-hydroxyphenyl)-3-{4-[2-(6-[(methoxyimino)(phenyl)methyl]-2-oxo-1,3-benzothiazol-3(2H)-yl)ethoxy]phenyl}propanoate 1.5 g of the compound obtained in Step B, in 50 ml of methanol and 0.1 ml of concentrated sulphuric acid, are heated at reflux for 2 hours. The solvent is then evaporated off, the residue is hydrolysed and the precipitate obtained is chromatographed on silica gel (eluant: AcOEt/toluene 5/95).

Melting point: 80–82° C.

2nd method:

Step A: Methyl 3-{4-[2-(6-benzoyl-2-oxo-1,3-benzothiazol-3(2H)-yl)ethoxy]phenyl}-2-(2-hydroxyphenyl)propanoate Starting from 6-benzoylbenzothiazolinone and methyl 3-[4-(2-chloroethoxy)phenyl]-2-(2-hydroxyphenyl)propanoate, the procedure is as in Step C of Example 1.

Melting point: 119–121° C.

Step B: Methyl 2-(2-hydroxyphenyl)-3-{4-[2-(6-[(methoxyimino)(phenyl)methyl]-2-oxo-1,3-benzothiazol-3(2H)-yl)ethoxy]phenyl}propanoate Starting from the compound obtained in Step A, the procedure is as in Step D of Example 1.

Melting point: 80–82° C.

EXAMPLE 24

2-(2-Hydroxyphenyl)-3-{4-[2-(6-(methoxyimino)(phenyl)methyl]-2-oxo-1,3-benzothiazol-3(2H)-yl)ethoxy]phenyl}propanoic acid The title compound is obtained after hydrolysis of the compound obtained in Example 23, using an NaOH/dioxane mixture.

EXAMPLE 25

Methyl 2-benzyl-3-{4-[2-(6-[(methoxyimino)(phenyl)methyl]-2-oxo-1,3-benzothiazol-3(2H)-yl)ethoxy]phenyl}propanoate Step A: Methyl 2-{4-[2-(6-benzoyl-2-oxo-1,3-benzothiazol-3(2H)-yl)ethoxy]benzyl}-3-phenylpropanoate The procedure is as in Step C of Example 1, replacing the methyl [(2-chloroethoxy)phenyl]-2-ethoxypropanoate by methyl 2-benzyl-3-[4-(2-chloroethoxy)-phenyl]propanoate.

The title compound is obtained in the form of a beige solid.

Melting point: 65–67° C.

Step B: Methyl 2-benzyl-3-{4-[2-(6-[(methoxyimino)(phenyl)methyl]-2-oxo-1,3-benzothiazol-3(2H)-yl)ethoxy]phenyl}propanoate Starting from the compound obtained in Step A, the procedure is as in Step B of Example 2, replacing the hydroxylamine by O-methylhydroxylamine.

EXAMPLE 26

Methyl 2-{4-[2-(6-[(methoxyimino)(phenyl)methyl]-2-oxo-1,3-benzothiazol-3(2H)-yl)ethoxy]benzyl}-4-phenylbutanoate Step A: Methyl 2-{4-[2-(6-benzoyl-2-oxo-1,3-benzothiazol-3(2H)-yl)ethoxy]benzyl}-4-phenylbutanoate The procedure is as in Step C of Example 1, replacing the [(2-chloroethoxy)phenyl]-2-ethoxypropanoate by methyl 2-[4-(2-chloroethoxy)benzyl]-4-phenylbutanoate.

White solid.

Melting point: 51–54° C.

Step B: Methyl 2-{4-[2-(6-[(methoxyimino)(phenyl)methyl]-2-oxo-1,3-benzothiazol-3(2H)-yl)ethoxy]benzyl}-4-phenylbutanoate Starting from the compound obtained in Step A, the procedure is as in Step B of Example 2, replacing the hydroxylamine by O-methylhydroxylamine. The two (Z) and (E) compounds are not separated.

White solid.

Melting point: 80–83° C.

EXAMPLE 27

Methyl 2-{4-[2-(6-[(hydroxyimino)(phenyl)methyl]-2-oxo-1,3-benzothiazol-3(2H)-yl)ethoxy]benzyl}4-phenylbutanoate Starting from the compound obtained in Step A of Example 26, the procedure is as in Step B of Example 2. The two (Z) and (E) compounds are not separated.
Beige solid.
Melting point: 58–60° C.

EXAMPLE 28

Methyl 2-{4-[2-(6[(hydroxyimino)(phenyl)methyl]-2-oxo-1,3-benzothiazol-3(2H)-yl)ethoxy]benzyl}-5-phenylpentanoate Step A: Methyl 2-{4-[2-(6-benzoyl-2-oxo-1,3-benzothiazol-3(2H)-yl)ethoxy]benzyl}-5-phenylpentanoate The procedure is as in Step C of Example 1, replacing the methyl 3-[4-(2-chloroethoxy)-phenyl]-2-ethoxypropanoate by methyl 2-[4-(2-chloroethoxy)benzyl]-5-phenylpentanoate.
Beige solid.
Melting point: 55–57° C.

Step B: Methyl 2-{4-[2-(6-[(hydroxyimino)(phenyl)methyl]-2-oxo-1,3-benzothiazol-3(2H)-yl)ethoxy]benzyl}-5-phenylpentanoate Starting from the compound obtained in Step A, the procedure is as in Step B of Example 2.

EXAMPLE 29

N-(tert-Butoxycarbonyl)-4-[2-(6-[(hydroxyimino)(phenyl)methyl]-2-oxo-1,3-benzothiazol-3(2H)-yl)ethoxy]phenylalanine The title compound is obtained by hydrolysis, in a basic medium, of the compound obtained in Example 11.
Melting point: Decomposition after 250° C.

EXAMPLE 30

N-(tert-Butoxycarbonyl)-4-[2-(6-[(methoxyimino)(phenyl)methyl]-2-oxo-1,3-benzothiazol-3(2H)-yl)ethoxy]phenylalanine The title compound is obtained by hydrolysis, in a basic medium, of the compound obtained in Example 10.

EXAMPLE 31

Ethyl 2-{4-[2-(6-[(methoxyimino)(phenyl)methyl]-2-oxo-1,3-benzothiazol-3(2H)-yl)ethoxy]phenoxy}-2-methylpropanoate Step A: Ethyl 2-{4-[2-(6-benzoyl-2-oxo-1,3-benzothiazol-3(2H)-yl)ethoxy]phenoxy}-2-methylpropanoate To a solution, heated at 80° C. for 2 hours, of 6-benzoyl-benzothiazolinone (6.7 mmol) in the presence of $K_2CO_3$ in 20 ml of DMF there is added ethyl 2-[4-(2-chloroethoxy)phenoxy]-2-methylpropanoate. The reaction mixture is heated at 120° C. for 5 days, cooled, hydrolysed using 100 ml of water and rendered alkaline using 1N NaOH. The precipitate obtained is filtered off and then recrystallised from cyclohexane to yield the title compound in the form of a white powder.
Melting point: 120–121° C.

Step B: Ethyl 2-{4-[2-(6-[(methoxyimino)(phenyl)methyl]-2-oxo-1,3-benzothiazol-3(2H)-yl)ethoxy]phenoxy}-2-methylpropanoate A solution of the compound obtained in Step A (500 mg) and O-methylhydroxylamine hydrochloride (165 mg) in 15 ml of pyridine is heated at reflux for 3 hours. The reaction mixture is hydrolysed using 100 ml of ice-cold water, acidified using 6N HCl and then extracted with ethyl acetate. The organic phase is dried over magnesium sulphate and evaporated to dryness under reduced pressure. The residue is then purified on silica gel, eluant AcOEt/PE 2/8, to yield the title compound in the form of a white oil (wax).

EXAMPLE 32

Ethyl 2-{4-[2-(6 [(hydroxyimino)(phenyl)methyl]-2-oxo-1,3-benzo-thiazol-3(2H)-yl)ethoxy]phenoxy}-2-methylpropanoate A solution of the compound obtained in Step A of Example 31 (500 mg) and hydroxylamine hydrochloride (137 mg) in 10 ml of pyridine is heated at reflux for 3 hours. The reaction mixture is hydrolysed using 100 ml of ice-cold water and is acidified using 6N HCl. The precipitate obtained is then filtered off, washed with water and then with petroleum ether and purified on silica gel (eluant AcOEt/PE 2/8) to yield the title compound in the form of a white powder.
Melting point: 60–62° C.

EXAMPLE 33

2-{4-[2-(6-[(Methoxyimino)(phenyl)methyl]-2-oxo-1,3-benzothiazol-3(2H)-yl)ethoxy]phenoxy}-2-methylpropanoic acid To a solution of the compound obtained in Step B of Example 31 (0.8 g) in 5 ml of ethanol 95° there is added potassium hydroxide (100 mg) dissolved in 1 ml of ethanol 95° The reaction mixture is heated at reflux overnight. After cooling to ambient temperature, the solution is acidified using 1N HCl. The precipitate obtained is then filtered and purified on a reverse phase, RP18, eluant MeOH/$H_2O$ 6/4, to yield the title compound in the form of a white powder.
Melting point: Decomposition after 170° C.

EXAMPLE 34

2-{4-[2-(6-[(Hydroxyimino)(phenyl)methyl]-2-oxo-1,3-benzothiazol-3(2H)-yl)ethoxy]phenoxy}-2-methylpropanoic acid To a solution of the compound obtained in Example 32 (0.5 g) in 5 ml of ethanol 95° there is added potassium hydroxide (107 mg) dissolved in 1 ml of ethanol 95°. The reaction mixture is heated at reflux overnight. After cooling to ambient temperature, the solution is acidified using 1N HCl. The precipitate obtained is then filtered and purified on a reverse phase, RP18, eluant MeOH/H$_2$O 6/4, to yield the title compound in the form of a white powder.

Melting point: Decomposition after 170° C.

EXAMPLE 35

Ethyl 2-{4-[2-(6-[(3-chlorophenyl)(methoxyimino)methyl]-2-oxo-1,3-benzothiazol-3(2M)-yl)ethoxy]phenoxy}-2-methylpropanoate Step A: Ethyl 2-{4-[2-(6-(3-chlorobenzoyl)-2-oxo-1,3-benzothiazol-3(2H)-yl)-ethoxy]phenoxy}-2-methylpropanoate To a solution, heated at 80° C. for 2 hours, of 6-(3'-chlorobenzoyl)-benzothiazolinone (1.8 g) in the presence of K$_2$CO$_3$ (1.72 g) in 20 ml of DMF there is added ethyl 2-[4-(2-chloroethoxy)phenoxy]-2-methylpropanoate (1.96 g). The reaction mixture is heated at 120° C. for 5 days, cooled, hydrolysed using 100 ml of water and rendered alkaline using 1N NaOH. The precipitate obtained is filtered off and then recrystallised from cyclohexane to yield the title compound in the form of a white powder.

Melting point: 125–126° C.

Step: Ethyl 2-{4-[2-(6-[(3-chlorophenyl)(methoxyimino)methyl]-2-oxo-1,3-benzothiazol-3(2H)-yl)ethoxy]phenoxy}-2-methylpropanoate A solution of the compound obtained in Step A (1.00 g) and O-methylhydroxylamine hydrochloride (309 mg) in 15 ml of pyridine is heated at reflux for 3 hours. The reaction mixture is hydrolysed using 100 ml of ice-cold water and acidified using 6N HCl. The precipitate obtained is filtered off, washed with water and then recrystallised from petroleum ether by cooling in a freezer to yield the title compound in the form of a white powder.

Melting point: 93–98° C.

EXAMPLE 36

2-{4-[2-(6-[(3-Chlorophenyl)(methoxyimino)methyl]-2-oxo-1,3-benzothiazol-3(2H)-yl)ethoxy]phenoxy}-2-methylpropanoic acid To a solution of the compound obtained in Example 35 (0.4 g) in 5 ml of ethanol 95° there is added potassium hydroxide (40 mg) dissolved in 1 ml of ethanol 95°. The reaction mixture is heated at reflux overnight. After cooling to ambient temperature, the solution is acidified using 1N HCl. The precipitate obtained is then filtered off and purified on a reverse phase, RP18, eluant MeOH/H$_2$O 6/4, to yield the title compound in the form of a white powder.

Melting point: decomposition starting from 230° C.

EXAMPLE 37

Ethyl 2-{4-[2-(6-[(3-chlorophenyl)(hydroxyimino)methyl]-2-oxo-1,3-benzothiazol-3(2H)-yl)ethoxy]phenoxy}-2-methylpropanoate A solution of the compound obtained in Step A of Example 35 (1.30 g) and hydroxylamine hydrochloride (335 mg) in 10 ml of pyridine is heated at reflux for 3 hours. The reaction mixture is hydrolysed using 100 ml of ice-cold water and acidified using 6N HCl. The precipitate obtained is then filtered, washed with water and then with petroleum ether and then purified on a reverse phase, RP18, eluant MeOH/H$_2$O 6/4, to yield the title compound in the form of a white powder.

EXAMPLE 38

2-{4-[2-(6-[(3-Chlorophenyl)(hydroxyimino)methyl]-2-oxo-1,3-benzothiazol-3(2H)-yl)ethoxy]phenoxy}-2-methylpropanoic acid To a solution of the compound obtained in Example 37 (0.6 g) in 5 ml of ethanol 95° there is added potassium hydroxide (90 mg) dissolved in 1 ml of ethanol 95°. The reaction mixture is heated at reflux overnight. After cooling to ambient temperature, the solution is acidified using 1N HCl. The precipitate obtained is then filtered and purified on a reverse phase, RP18, eluant MeOH/H$_2$O 6/4, to yield the title compound in the form of a white powder.

Melting point: decomposition starting from 170° C.

EXAMPLE 39

Ethyl 5-{4-[2-(6-[(hydroxyimino)(phenyl)methyl]-2-oxo-1,3-benzo-thiazol-3(2H)-yl)ethoxy]phenoxy}-2,2-dimethylpentanoate Step A: Ethyl 5-{4-[2-(6-benzoyl-2-oxo-1,3-benzothiazol-3(2H)-yl)ethoxy]phenoxy}-2,2-dimethylpentanoate To a solution, heated at 80° C. for 2 hours, of 6-benzoyl-benzothiazolinone (1 g) in the presence of K$_2$CO$_3$ (1.08 g) in 10 ml of DMF there is added ethyl 5-[4-(2-chloroethoxy)phenoxy]-2,2-dimethylpentanoate (1.41 g). The reaction mixture is heated at 120° C. for 5 days and is then hydrolysed using 100 ml of water. The solution is extracted with ethyl acetate, dried over magnesium sulphate and then evaporated to dryness under reduced pressure. The residue is purified over silica gel, eluant AcOEt/PE 2/8, to yield the title compound in the form of a white powder.

Melting point: 82–84° C.

Step B: Ethyl 5-{4-[2-(6-[(hydroxyimino)(phenyl)methyl]-2-oxo-1,3-benzothiazol-3(2H)-yl)ethoxy]phenoxy}-2,2-dimethylpentanoate Starting from the compound obtained in Step A, the procedure is as in Example 37.

Melting point: 66–68° C.

EXAMPLE 40

{4-[2-(6-[(Hydroxyimino)(phenyl)methyl]-2-oxo-1,3-benzothiazol-3(2H)-yl)ethoxy]phenyl}acetonitrile Step A: {4-[2-(6-Benzoyl-2-oxo-1,3-benzothiazol-3(2H)-yl)ethoxy]phenyl}-acetonitrile The procedure is as in Step C of Example 1, replacing the methyl 3-[4-(2-chloroethoxy)-phenyl]-2-ethoxypropanoate by [4-(2-chloroethoxy)phenyl]acetonitrile.

White solid.

Melting point: 160–162° C.

Step B: {4-[2-(6-[(Hydroxyimino) (phenyl)methyl]-2-oxo-1,3-benzothiazol-3(2H)-yl)ethoxy]phenyl}acetonitrile Starting from the compound obtained in Step A, the procedure is as in Example 37.

EXAMPLE 41

3-{4-[2-(6-[(Hydroxyimino)(phenyl)methyl]-2-oxo-1,3-benzothiazol-3(2H)-yl)ethoxy]phenyl}propanenitrile Step A: 3-{4-[2-(6-Benzoyl-2-oxo-1,3-benzothiazol-3(2H)-yl)ethoxy]phenyl}-propanenitrile The procedure is as in Step C of Example 1, replacing the methyl 3-[4-(2-chloroethoxy)-phenyl]-2-ethoxypropanoate by 3-[4-(2-chloroethoxy)phenyl]propanenitrile.
White solid.
Melting point: 106–108° C.

Step B: 3-{4-[2-(6-[(Hydroxyimino)(phenyl)methyl]-2-oxo-1,3-benzothiazol-3(2H)-yl)ethoxy]phenyl}propanenitrile Starting from the compound obtained in Step A, the procedure is as in Example 37.

EXAMPLE 42

6-[(Hydroxyimino)(phenyl)methyl]-3-{2-[4-(1H-tetrazol-5-ylmethyl)-phenoxy]ethyl}-1,3-benzothiazol-2(3H)-one Step A: 6-Benzoyl-3-{2-[4-(1H-tetrazol-5-ylmethyl)phenoxy]ethyl}-1,3-benzothiazol-2(3H)-one The procedure is as in Step C of Example 1, replacing the methyl 3-[4-(2-chloroethoxy)phenyl]-2-ethoxypropanoate by 5-[4-(2-chloroethoxy)benzyl]-1H-tetrazole.
White solid.
Melting point: 140–142° C.

Step B: 6-[(Hydroxyimino)(phenyl)methyl]-3-{2-[4-(1H-tetrazol-5-ylmethyl)phenoxy]ethyl}-1,3-benzothiazol-2(3H)-one Starting from the compound obtained in Step A, the procedure is as in Example 37.

EXAMPLE 43

6-[(Hydroxyimino)(phenyl)methyl]-3-(2-{4-[2-(1H-tetrazol-5-yl)ethyl]phenoxy}ethyl)-1,3-benzothiazol-2(3H)-one Step A: 6-Benzoyl-3-(2-{4-[2-(1H-tetrazol-5-yl)ethyl]phenoxy}ethyl)-1,3-benzothiazol-2(3H)-one The procedure is as in Step C of Example 1, replacing the methyl 3-[4-(2-chloroethoxy)phenyl]-2-ethoxypropanoate by 5-{2-[4-(2-chloroethoxy)phenyl]ethyl}-1H-tetrazole.
White solid.
Melting point: 120–124° C.

Step B: 6-[(Hydroxyimino)(phenyl)methyl]-3-(2-{4-[2-(1H-tetrazol-5-yl)ethyl]phenoxy}ethyl)-1,3-benzothiazol-2(3H)-one Starting from the compound obtained in Step A, the procedure is as in Example 37.

EXAMPLE 44 tert-Butyl 2-{4-[2-(6-[(hydroxyimino)(phenyl)methyl]-2-oxo-1,3-benzothiazol-3(2H)-yl)ethoxy]phenyl}ethylcarbamate Step A: tert-Butyl 2-{4-[2-(6-benzoyl-2-oxo-1,3-benzothiazol-3(2H)-yl)ethoxy]-phenyl}ethylcarbamate The procedure is as in Step C of Example 1, replacing the methyl 3-[4-(2-chloroethoxy)-phenyl]-2-ethoxypropanoate by tert-butyl 2-[4-(2-chloroethoxy)phenyl]ethylcarbamate.
White solid.
Melting point: 114–116° C.

Step B: tert-Butyl 2-{4-[2-(6-[(hydroxyimino)(phenyl)methyl]-2-oxo-1,3-benzothiazol-3(2H)-yl)ethoxy]phenyl}ethylcarbamate Starting from the compound obtained in Step A, the procedure is as in Example 37.

EXAMPLE 45

N-(2-{4-[2-(6-[(Hydroxyimino)(phenyl)methyl]-2-oxo-1,3-benzothiazol-3(2H)-yl)ethoxy]phenyl}ethyl)acetamide Step A: N-(2-{4-[2-(6-Benzoyl-2-oxo-1,3-benzothiazol-3(2H)-yl)ethoxy]phenyl}-ethyl)acetamide The procedure is as in Step C of Example 1, replacing the methyl 3-[4-(2-chloroethoxy)-phenyl]-2-ethoxypropanoate by N-{2-[4-(2-chloroethoxy)phenyl]ethyl}acetamide.
White solid.
Melting point: 108–110° C.

Step B: N-(2-{4-[2-(6-[(Hydroxyimino)(phenyl)methyl]-2-oxo-1,3-benzothiazol-3(2H)-yl)ethoxy]phenyl}ethyl)acetamide Starting from the compound obtained in Step A, the procedure is as in Example 37.

EXAMPLE 46

Ethyl 2-{4-[2-(6-[(methoxyimino)(phenyl)methyl]-2-oxo-1,3-benzothiazol-3(2H)-yl)ethoxy]phenoxy}propanoate Step A: Ethyl 2-{4-[2-(6-benzoyl-2-oxo-1,3-benzothiazol-3(2H)-yl)ethoxy]phenoxy}-propanoate The procedure is as in Step C of Example 1, replacing the methyl [(2-chloroethoxy)-phenyl]-2-ethoxypropanoate by ethyl 2-[4-(2-chloroethoxy)phenoxy]propanoate.
White solid.
Melting point: 100–101 C.

Step B. Ethyl 2-{4-[2-(6-[(methoxyimino)(phenyl)methyl]-2-oxo-1,3-benzothiazol-3(2H)-yl)ethoxy]phenoxy}propanoate Starting from the compound obtained in Step A, the procedure is as in Step B of Example 2, replacing the hydroxylamine by O-methylhydroxylamine.

EXAMPLE 47

Ethyl 2-{4-[2-(6-[(methoxyimino)(phenyl)methyl]-2-oxo-1,3-benzothiazol-3(2H)-yl)ethoxy]phenoxy}butanoate Step A: Ethyl 2-{4-[2-(6-benzoyl-2-oxo-1,3-benzothiazol-3(2H)-yl)ethoxy]phenoxy}-butanoate The procedure is as in Step C of Example 1, replacing the methyl [(2-chloroethoxy)-phenyl]-2-ethoxypropanoate by ethyl 2-[4-(2-chloroethoxy)phenoxy]butanoate.
White solid.
Melting point: 113–114° C.

Step B: Ethyl 2-{4-[2-(6-[(methoxyimino)(phenyl)methyl]-2-oxo-1,3-benzothiazol-3(2H)-yl)ethoxy]phenoxy}butanoate Starting from the compound obtained in Step A, the procedure is as in Step B of Example 2, replacing the hydroxylamine by O-methylhydroxylamine.

EXAMPLE 48

2-{4-[2-(6[(Hydroxyimino)(phenyl)methyl]-2-oxo-1,3-benzothiazol-3(2H)-yl)ethoxy]phenoxy}propanoic acid Step A: 2-{4-[2-(6-Benzoyl-2-oxo-1,3-benzothiazol-3(2H)-yl)ethoxy]phenoxy}-propanoic acid Starting from the compound obtained in Step A of Example 46, the procedure is as in Example 33.
White solid.
Melting point: 159–160° C.

Step B: 2-{4-[2-(6-[(Hydroxyimino)(phenyl)methyl]-2-oxo-1,3-benzothiazol-3(2H)-yl)ethoxy]phenoxy}propanoic acid Starting from the compound obtained in Step A, the procedure is as in Step B of Example 2.

EXAMPLE 49

Ethyl 2-{4-[2-(6-[N-methoxyethanimidoyl]-2-oxo-1,3-benzothiazol-3(2H)-yl)ethoxy]phenoxy}-2-methylpropanoate Step A: Ethyl 2-{4-[2-(6-acetyl-2-oxo-1,3-benzothiazol-3(2H)-yl)ethoxy]phenoxy}-2-methylpropanoate The procedure is as in Step C of Example 1, replacing the methyl [(2-chloroethoxy)-phenyl]-2-ethoxypropanoate by ethyl 2-[4-(2-chloroethoxy)phenoxy]-2-methylpropanoate, and replacing the 6-benzoylbenzothiazolinone by 6-acetyl-benzothiazolinone.
White solid.
Melting point: 112–113° C.

Step B: Ethyl 2-{4-[2-(6-[N-methoxyethanimidoyl]-2-oxo-1,3-benzothiazol-3(2H)-yl)ethoxy]phenoxy}-2-methylpropanoate Starting from the compound obtained in Step A, the procedure is as in Step B of Example 2, replacing the hydroxylamine by O-methylhydroxylamine. The two (Z) and (E) compounds are not separated.
Colourless oil.

EXAMPLE 50

2-{4-[2-(6-[N-Methoxyethanimidoyl]-2-oxo-1,3-benzothiazol-3(2H)-yl)ethoxy]phenoxy}-2-methylpropanoic acid 1st Method
Starting from the compound obtained in Example 49, the procedure is as in Example 33.
White solid.
Melting point: 145–148° C.
2nd Method:

Step A: 2-{4-[2-(6-Acetyl-2-oxo-1,3-benzothiazol-3(2H)-yl)ethoxy]phenoxy}-2-methylpropanoic acid Starting from the compound obtained in Step A of Example 49, the procedure is as in Example 33.
Melting point: 175.5–177.5° C.

Step B: 2-{4-[2-(6-[N-Methoxyethanimidoyl]-2-oxo-1,3-benzothiazol-3(2H)-yl)ethoxy]phenoxy}-2-methylpropanoic acid Starting from the compound obtained in Step A, the procedure is as in Step D of Example 1.
White solid.
Melting point: 145–148° C.

EXAMPLE 51

Ethyl 2-{4-[2-(6-[N-hydroxyethanimidoyl]-2-oxo-1,3-benzothiazol-3(2H)-yl)ethoxy]phenoxy}-2-methylpropanoate Starting from the compound obtained in Step A of Example 49, the procedure is as in Step B of Example 2.

EXAMPLE 52

2-{4-[2-(6-[N-Hydroxyethanimidoyl]-2-oxo-1,3-benzothiazol-3(2H)-yl)ethoxy]phenoxy}-2-methylpropanoic acid Starting from the compound obtained in Example 51, the procedure is as in Example 33.
White solid.
Melting point: 185–187° C.

EXAMPLE 53

Methyl 3-{4-[2-(6-[cyclopropyl(hydroxyimino)methyl]-2-oxo-1,3-benzothiazol-3(2H)-yl)ethoxy]phenyl}-2-ethoxypropanoate Step A: Methyl 3-{4-[2-(6-(cyclopropylcarbonyl)-2-oxo-1,3-benzothiazol-3(2H)-yl)ethoxy]phenyl}-2-ethoxypropanoate The procedure is as in Step C of Example 1, replacing the 6-benzoylbenzothiazolinone by 6-(cyclopropylcarbonyl)benzothiazolinone.
Melting point: 97–98° C.

Step B: Methyl 3-{4-[2-(6-[cyclopropyl(hydroxyimino)methyl]-2-oxo-1,3-benzothiazol-3(2H)-yl)ethoxy]phenyl}-2-ethoxypropanoate Starting from the compound obtained in Step A, the procedure is as in Step B of Example 2.

EXAMPLE 54

Methyl 3-{4-[2-(6-[(3-chlorophenyl)(methoxyimino)methyl]-2-oxo-1,3-benzothiazol-3(2H)-yl)ethoxy]phenyl}-2-ethoxypropanoate Step A: Methyl 3-{4-[2-(6-(3-chlorobenzoyl)-2-oxo-1,3-benzothiazol-3(2H)-yl)ethoxy]phenyl}-2-ethoxypropanoate The procedure is as in Step C of Example 1, replacing the 6-benzoylbenzothiazolinone by 6-(3-chlorobenzoyl)benzothiazolinone.

Step B: Methyl 3-{4-[2-(6-[(3-chlorophenyl)(methoxyimino)methyl]-2-oxo-1,3-benzothiazol-3(2H)-yl)ethoxy]phenyl}-2-ethoxypropanoate Starting from the compound obtained in Step A, the procedure is as in Step B of Example 2, replacing the hydroxylamine by O-methylhydroxylamine.

EXAMPLE 55

3-{4-[2-(6-[(3-Chlorophenyl)(methoxyimino)methyl]-2-oxo-1,3-benzothiazol-3(2H)-yl)ethoxy]phenyl}-2-ethoxypropanoic acid Starting from the compound obtained in Example 53, the procedure is as in Example 33.
Melting point: 96–98° C.

EXAMPLE 56

Methyl 3-{4-[2-(6 [(3-chlorophenyl)(hydroxyimino)methyl]-2-oxo-1,3-benzothiazol-3(2H)-yl)ethoxy]phenyl}-2-ethoxypropanoate The procedure is as in Example 54 replacing in stage B the O-methylhydroxylamine by the hydroxylamine.

EXAMPLE 57

Methyl 3-{4-[2-(6-[(tert-butoxyimino)(phenyl)methyl]-2-oxo-1,3-benzothiazol-3(2H)-yl)ethoxy]phenyl}-2-ethoxypropanoate Starting from the compound obtained in Step C of Example 1, the procedure is as in Step B of Example 2, replacing the hydroxylamine by O-(tert-butyl)hydroxylamine.

EXAMPLE 58

3-{4-[2-(6-[(tert-Butoxyimino)(phenyl)methyl]-2-oxo-1,3-benzo-thiazol-3(2H)-yl)ethoxy]phenyl}-2-ethoxypropanoic acid Starting from the compound obtained in Example 57, the procedure is as in Example 33.
Melting point: 80–81° C.

EXAMPLE 59

Methyl 3-{4-[2-(6-[[(benzyloxy)imino](phenyl)methyl]-2-oxo-1,3-benzothiazol-3(2H)-yl)ethoxy]phenyl}-2-ethoxypropanoate Starting from the compound obtained in Step C of Example 1, the procedure is as in Step B of Example 2, replacing the hydroxylamine by O-benzylhydroxylamine.

EXAMPLE 60

3-{4-[2-(6-[[(Benzyloxy)imino](phenyl)methyl]-2-oxo-1,3-benzothiazol-3(2H)-yl)ethoxy]phenyl}-2-ethoxypropanoic acid Starting from the compound obtained in Example 59, the procedure is as in Example 33.
Melting point: 105–106° C.

EXAMPLE 61

3-{4-[2-(6-[(Z)-(3-Chlorophenyl)(methoxyimino)methyl]-2-oxo-1,3-benzothiazol-3(2H)-yl)ethoxy]phenyl}-2-ethoxypropanoic acid Starting from the compound obtained in Example 7, the procedure is as in Example 33.
Melting point: 96–98° C.

EXAMPLE 62

3-{4-[2-(6-[(Methoxyimino)(phenyl)methyl]-2-oxo-1,3-benzothiazol-3(2H)-yl)ethoxy]phenyl}-2-(2,2,2-trifluoroethoxy)propanoic acid Starting from the compound obtained in Example 3, the procedure is as in Example 33.
Melting point: 56–57° C.

EXAMPLE 62a

3-{4-[2-(6-[(E)-(Methoxyimino)(phenyl)methyl]-2-oxo-1,3-benzothiazol-3(2H)-yl)ethoxy]phenyl}-2-(2,2,2-trifluoroethoxy)propanoic acid The compound obtained in Example 62 is taken up in diethyl ether. The title compound is precipitated selectively and filtered off.

Starting from the compound obtained in Example 62a, Examples 62a(1) and 62a(2) are obtained by chiral separation on CHIRALPAK AD, using a mixture of methanol/water/trifluoroacetic acid (1000/5/1) and detection at 285 nm.

EXAMPLE 62a(1)

3-{4-[2-(6-[(E)-(Methoxyimino)(phenyl)methyl]-2-oxo-1,3-benzothiazol-3(2H)-yl)ethoxy]phenyl}-2-(2,2,2-trifluoroethoxy)-propanoic acid, enantiomer 1

The title compound is obtained with an optical purity greater than 99%.

EXAMPLE 62a(2)

3-{4-[2-(6-[(E)-(Methoxyimino)(phenyl)methyl]-2-oxo-1,3-benzothiazol-3(2H)-yl)ethoxy]phenyl}-2-(2,2,2-trifluoroethoxy)-propanoic acid, enantiomer 2

The title compound is obtained with an optical purity greater than or equal to 98%.

EXAMPLE 62b

3-{4-[2-(6-[(Z)-(Methoxyimino)(phenyl)methyl]-2-oxo-1,3-benzothiazol-3(2H)-yl)ethoxy]phenyl}-2-(2,2,2-trifluoroethoxy)-propanoic acid The compound obtained in Example 62 is taken up in the diethyl ether. The filtrate is recovered and evaporated to yield the title compound.

Starting from the compound obtained in Example 62b, Examples 62b(1) and 62b(2) are obtained by separation on a chiral column.

EXAMPLE 62b(1)

3-{4-[2-(6-[(Z)-(Methoxyimino)(phenyl)methyl]-2-oxo-1,3-benzothiazol-3(2H)-yl)ethoxy]phenyl}-2-(2,2,2-trinfluoroethoxy)-propanoic acid, enantiomer 1

EXAMPLE 62b(2)

3-{4-[2-(6-[(Z)-(Methoxyimino)(phenyl)methyl]-2-oxo-1,3-benzothiazol-3(2H)-yl)ethoxy]phenyl}-2-(2,2,2-trifluoroethoxy)-propanoic acid, enantiomer 2

EXAMPLE 63

Methyl 2-isopropoxy-3-{4-[2-(6-[(methoxyimino)(phenyl)methyl]-2-oxo-1,3-benzothiazol-3(2H)-yl)ethoxy]phenyl}propanoate Step A: Methyl 3-{4-[2-(6-benzoyl-2-oxo-1,3-benzothiazol-3(2H)-yl)ethoxy]phenyl}-2-isopropoxypropanoate The procedure is as in Example 1, Steps A, B and C, replacing the methyl 2-ethoxy-2-diethylphosphonoacetate in Step A by methyl 2-isopropoxy-2-diethylphosphonoacetate.

Step B: Methyl 2-isopropoxy-3-{4-[2-(6-[(methoxyimino)(phenyl)methyl]-2-oxo-1,3-benzothiazol-3(2H)-yl)ethoxy]phenyl}propanoate Starting from the compound obtained in Step A, the procedure is as in Step D of Example 1.

EXAMPLE 64

2-Isopropoxy-3-{4-[2-(6-[(methoxyimino)(phenyl)methyl]-2-oxo-1,3-benzothiazol-3(2H)-yl)ethoxy]phenyl}propanoic acid Starting from the compound obtained in Example 63, the procedure is as in Example 33.

Melting point: 72–74° C.

EXAMPLE 65

Ethyl 3-{4-[2-(6-[(3-bromophenyl)(methoxyimino)methyl]-2-oxo-1,3-benzothiazol-3(2H)-yl)ethoxy]phenyl}-2-ethoxypropanoate Step A: Ethyl 3-{4-[2-(6-(3-bromobenzoyl)-2-oxo-1,3-benzothiazol-3(2H)-yl)-ethoxy]phenyl}-2-ethoxypropanoate The procedure is as in Example 1, Steps A, B and C, replacing the methyl 2-ethoxy-2-diethylphosphonoacetate in Step A by ethyl 2-ethoxy-2-diethylphosphonoacetate and replacing the 6-benzoylbenzothiazolinone in Step C by 6-(3-bromobenzoyl)benzo-thiazolinone.

Step B: Ethyl 3-{4-[2-(6-[(3-bromophenyl)(methoxyimino)methyl-2-oxo-1,3-benzothiazol-3(2H)-yl)ethoxy]phenyl}-2-ethoxypropanoate Starting from the compound obtained in Step A, the procedure is as in Step D of Example 1.

Oil.

EXAMPLE 66

Ethyl 3-{4-[2-(6-[(Z)-(3-bromophenyl)(methoxyimino)methyl]-2-oxo-1,3-benzothiazol-3(2H)-yl)ethoxy]phenyl}-2-ethoxypropanoate The compound obtained in Example 65 is taken up in diethyl ether and the title compound is precipitated in selective manner and filtered to yield the (Z) isomer.

Melting point: 86–88° C.

EXAMPLE 67

Ethyl 5-{4-[2-(6-[(methoxyimino)(phenyl)methyl]-2-oxo-1,3-benzo-thiazol-3(2H)-yl)ethoxy]phenoxy}-2,2-dimethylpentanoate Starting from the compound obtained in Step A of Example 39, the procedure is as in Step D of Example 1.

Melting point: 82–84° C.

EXAMPLE 68

5-{4-[2-(6-[(Methoxyimino)(phenyl)methyl]-2-oxo-1,3-benzothiazol-3(2H)-yl)ethoxy]phenoxy}-2,2-dimethylpentanoic acid 1st Method:
Starting from the compound obtained in Example 67, the procedure is as in Example 33.
Melting point: 127–129° C.
2nd Method:

Step A: 5-{4-[2-(6-Benzoyl-2-oxo-1,3-benzothiazol-3(2H)-yl)ethoxy]phenoxy}-2,2-dimethylpentanoic acid Starting from the compound obtained in Step A of Example 39, the procedure is as in Example 33.
Melting point: 90–92° C.

Step B: 5-{4-[2-(6-[(Methoxyimino) (phenyl)methyl]-2-oxo-1,3-benzothiazol-3(2H)-yl)ethoxy]phenoxy}-2,2-dimethylpentanoic acid Starting from the compound obtained in Step A, the procedure is as in Step D of Example 1.
Melting point: 127–129° C.

EXAMPLE 69

3-{4-[2-(6-[(3-Bromophenyl)(methoxyimino)methyl]-2-oxo-1,3-benzothiazol-3(2H)-yl)ethoxy]phenyl}-2-ethoxypropanoic acid Starting from the compound obtained in Example 65, the procedure is as in Example 33.
Melting point: 58–60° C.

EXAMPLE 70

3-{4-[2-(6-[(Z)-(3-Bromophenyl)(methoxyimino)methyl]-2-oxo-1,3-benzothiazol-3(2H)-yl)ethoxy]phenyl}-2-ethoxypropanoic acid The compound obtained in Example 69 is taken up in diethyl ether and the title compound is precipitated in selective manner and filtered off to yield the (Z) isomer.
Melting point: 74–76° C.

EXAMPLE 71

5-{4-[2-(6-[(Hydroxyimino)(phenyl)methyl]-2-oxo-1,3-benzothiazol-3(2H)-yl)ethoxy]phenoxy}-2,2-dimethylpentanoic acid Starting from the compound obtained in Example 39, the procedure is as in Example 33.
Melting point: 148–150° C.

EXAMPLE 72

Ethyl 3-{4-[2-(6-[(2-bromophenyl)(methoxyimino)methyl]-2-oxo-1,3-benzothiazol-3(2H)-yl)ethoxy]phenyl}-2-ethoxypropanoate Step A: Ethyl 3-{4-[2-(6-(2-bromobenzoyl)-2-oxo-1,3-benzothiazol-3(2H)-yl)-ethoxy]phenyl}-2-ethoxypropanoate The procedure is as in Example 1, Steps A, B and C, replacing the methyl 2-ethoxy-2-diethylphosphonoacetate in Step A by ethyl 2-ethoxy-2-diethylphosphonoacetate and replacing the 6-benzoylbenzothiazolinone in Step C by 6-(2-bromobenzoyl)benzothiazolinone.
Oil.

Step B: Ethyl 3-{4-[2-(6-[(2-Bromophenyl)(methoxyimino)methyl]-2-oxo-1,3-benzothiazol-3(2H)-yl)ethoxy]phenyl}-2-ethoxypropanoate Starting from the compound obtained in Step A, the procedure is as in Step D of Example 1.
Oil.

EXAMPLE 73

3-{4-[2-(6-[(2-Bromophenyl)(methoxyimino)methyl]-2-oxo-1,3-benzothiazol-3(2H)-yl)ethoxy]phenyl}-2-ethoxypropanoic acid 1st Method:
Starting from the compound obtained in Example 72, the procedure is as in Example 33.
2nd Method:

Step A: 3-{4-[2-(6-(2-Bromobenzoyl)-2-oxo-1,3-benzothiazol-3(2H)-yl)ethoxy]-phenyl}-2-ethoxypropanoic acid Starting from the compound obtained in Step A of Example 72, the procedure is as in Example 33.
Melting point: 64–66° C.

Step B: 3-{4-[2-(6-[(2-Bromophenyl)(methoxyiminomethyl]-2-oxo-1,3-benzothiazol-3(2H)-yl)ethoxy]phenyl}-2-ethoxypropanoic acid Starting from the compound obtained in Step A, the procedure is as in Step D of Example 1.

EXAMPLE 74

Methyl 2-{4-[3-(6-[(methoxyimino)(phenyl)methyl]-2-oxo-1,3-benzothiazol-3(2H)-yl)propoxy]phenoxy}-2-methylpropanoate Step A: Methyl 2-{4-[3-(6-benzoyl-2-oxo-1,3-benzothiazol-3(2H)-yl)propoxy]-phenoxy}-2-methylpropanoate The procedure is as in Step A of Example 31, replacing the ethyl 2-[4-(2-chloroethoxy)phenoxy]-2-methylpropanoate by methyl 2-[4-(3-chloropropoxy)phenoxy]-2-methylpropanoate.

Step B: Methyl 2-{4-[3-(6-[(methoxyimino)(phenyl)methyl]-2-oxo-1,3-benzothiazol-3(2H)-yl)propoxy]phenoxy}-2-methylpropanoate Starting from the compound obtained in Step A, the procedure is as in Step D of Example 1.

EXAMPLE 75

2-{4-[3-(6[(Methoxyimino)(phenyl)methyl]-2-oxo-1,3-benzothiazol-3(2H)-yl)propoxy]phenoxy}-2-methylpropanoic acid 1st Method
Starting from the compound obtained in Example 74, the procedure is as in Example 33.
2nd Method:

Step A: 2-{4-[3-(6-Benzoyl-2-oxo-1,3-benzothiazol-3(2H)-yl)propoxy]phenoxy}-2-methylpropanoic acid Starting from the compound obtained in Step A of Example 74, the procedure is as in Example 33.
Melting point: 121–122° C.

Step B: 2-{4-[3-(6-[(Methoxyimino) (phenyl)methyl]-2-oxo-1,3-benzothiazol-3(2H)-yl)propoxy]phenoxy}-2-methylpropanoic acid Starting from the compound obtained in Step A, the procedure is as in Step D of Example 1.

EXAMPLE 76

Methyl 2-{3-[3-(6-[(methoxyimino)(phenyl)methyl]-2-oxo-1,3-benzothiazol-3(2H)-yl)propoxy]phenoxy}-2-methylpropanoate Step A: Methyl 2-{3-[3-(6-benzoyl-2-oxo-1,3-benzothiazol-3(2H)-yl)propoxy]-phenoxy}-2-methylpropanoate The procedure is as in Step A of Example 31, replacing the ethyl 2-[4-(2-chloroethoxy)-phenoxy]-2-methylpropanoate by methyl 2-[3-(3-chloropropoxy)phenoxy]-2-methylpropanoate.

Step B: Methyl 2-{3-[3-(6-[(methoxyimino)(phenyl)methyl]-2-oxo-1,3-benzothiazol-3(2H)-yl)propoxy]phenoxy}-2-methylpropanoate Starting from the compound obtained in Step A, the procedure is as in Step D of Example 1.

EXAMPLE 77

2-{3-[3-(6-[(Methoxyimino)(phenyl)methyl]-2-oxo-1,3-benzothiazol-3(2H)-yl)propoxy]phenoxy}-2-methylpropanoic acid 1 st Method:
Starting from the compound obtained in Example 76, the procedure is as in Example 33.

2nd Method:

Step A 2-{3-[3-(6-Benzoyl-2-oxo-1,3-benzothiazol-3(2H)-yl)propoxy]phenoxy}-2-methylpropanoic acid Starting from the compound obtained in Step A of Example 76, the procedure is as in Example 33.
Melting point: 79–80° C.

Step B: 2-{3-[3-(6-[(Methoxyimino)(phenyl)methyl]-2-oxo-1,3-benzothiazol-3(2H)-yl)propoxy]phenoxy}-2-methylpropanoic acid Starting from the compound obtained in Step A, the procedure is as in Step D of Example 1.

EXAMPLE 78

Methyl 2-{3-[4-(6-[(methoxyimino)(phenyl)methyl]-2-oxo-1,3-benzothiazol-3(2H)-yl)butoxy]phenoxy}-2-methylpropanoate Step A: Methyl 2-{3-[4-(6-benzoyl-2-oxo-1,3-benzothiazol-3(2H)-yl)butoxy]-phenoxy}-2-methylpropanoate The procedure is as in Step A of Example 31, replacing the ethyl 2-[4-(2-chloroethoxy)-phenoxy]-2-methylpropanoate by methyl 2-[3-(4-chlorobutoxy)phenoxy]-2-methylpropanoate.

Step B: Methyl 2-{3-[4-(6-[(methoxyimino)(phenyl)methyl]-2-oxo-1,3-benzothiazol-3(2H)-yl)butoxy]phenoxy}-2-methylpropanoate Starting from the compound obtained in Step A, the procedure is as in Step D of Example 1.

EXAMPLE 79

2-{3-[4-(6[(Methoxyimino)(phenyl)methyl]-2-oxo-1,3-benzothiazol-3(2H)-yl)butoxy]phenoxy}-2-methylpropanoic acid 1 st Method:
Starting from the compound obtained in Example 78, the procedure is as in Example 33.
2nd Method:

Step A: 2-{3-[4-(6-Benzoyl-2-oxo-1,3-benzothiazol-3(2H)-yl)butoxy]phenoxy}-2-methylpropanoic acid Starting from the compound obtained in Step A of Example 78, the procedure is as in Example 33.
Melting point: 70–71° C.

Step B: 2-{3-[4-(6-[(Methoxyimino)(phenyl)methyl]-2-oxo-1,3-benzothiazol-3(2H)-yl)butoxy]phenoxy}-2-methylpropanoic acid Starting from the compound obtained in Step A, the procedure is as in Step D of Example 1.

EXAMPLE 80

Ethyl 2-{4-[3-(6-[(methoxyimino)(phenyl)methyl]-2-oxo-1,3-benzothiazol-3(2H)-yl)propoxy]phenoxy}-2-methylpropanoate Step A: Ethyl 2-{4-[3-(6-benzoyl-2-oxo-1,3-benzothiazol-3(2H)-yl)propoxy]phenoxy}-2-methylpropanoate The procedure is as in Step A of Example 31, replacing the ethyl 2-[4-(2-chloroethoxy)phenoxy]-2-methylpropanoate by ethyl 2-[4-(3-chloropropoxy)phenoxy]-2-methylpropanoate.

Wax.

Step B: Ethyl 2-{4-[3-(6-[(methoxyimino)(phenyl)methyl]-2-oxo-1,3-benzothiazol-3(2H)-yl)propoxy]phenoxy}-2-methylpropanoate Starting from the compound obtained in Step A, the procedure is as in Step D of Example 1.

EXAMPLE 81

Ethyl 2-{3-[4-(6-[(methoxyimino)(phenyl)methyl]-2-oxo-1,3-benzothiazol-3(2H)-yl)butoxy]phenoxy}-2-methylpropanoate Step A: Ethyl 2-{3-[4-(6-benzoyl-2-oxo-1,3-benzothiazol-3(2H)-yl)butoxy]phenoxy}-2-methylpropanoate The procedure is as in Step A of Example 31, replacing the ethyl 2-[4-(2-chloroethoxy)phenoxy]-2-methylpropanoate by ethyl 2-[3-(4-chlorobutoxy)phenoxy]-2-methylpropanoate.

Melting point: 99–101° C.

Step B: Ethyl 2-{3-[4-(6-[(methoxyimino)(phenyl)methyl]-2-oxo-1,3-benzothiazol-3(2H)-yl)butoxy]phenoxy}-2-methylpropanoate Starting from the compound obtained in Step A, the procedure is as in Step D of Example 1.

EXAMPLE 82

Ethyl 2-{3-[3-(6 (methoxyimino)(phenyl)methyl]-2-oxo-1,3-benzothiazol-3(2M)-yl)propoxy]phenoxy}-2-methylpropanoate Step A: Ethyl 2-{3-[3-(6-benzoyl-2-oxo-1,3-benzothiazol-3(2H)-yl)propoxy]-phenoxy}-2-methylpropanoate The procedure is as in Step A of Example 31, replacing the ethyl 2-[4-(2-chloroethoxy)phenoxy]-2-methylpropanoate by ethyl 2-[3-(3-chloropropoxy)phenoxy]-2-methylpropanoate.

Wax.

Step B: Ethyl 2-{3-[3-(6-[(methoxyimino)(phenyl)methyl]-2-oxo-1,3-benzothiazol-3(2H)-yl)propoxy]phenoxy}-2-methylpropanoate Starting from the compound obtained in Step A, the procedure is as in Step D of Example 1.

EXAMPLE 83

N-Butyryl-4-[2-(6-[(hydroxyimino)(phenyl)methyl]-2-oxo-1,3-benzothiazol-3(2H)-yl)ethoxy]phenylalanine Step A: 4-[2-(6-Benzoyl-2-oxo-1,3-benzothiazol-3(2H)-yl)ethoxy]-N-butyrylphenyl-alanine Starting from the compound obtained in Step A of Example 16, the procedure is as in Example 33.

Melting point: 146–148° C.

Step B: N-Butyryl-4-[2-(6-[(hydroxyimino)(phenyl)methyl]-2-oxo-1,3-benzothiazol-3(2H)-yl)ethoxy]phenylalanine Starting from the compound obtained in Step A, the procedure is as in Step B of Example 2.

EXAMPLE 84

Methyl 2-{4-[2-(6[(methoxyimino)(phenyl)methyl]-2-oxo-1,3-benzothiazol-3(2H)-yl)ethoxy]phenoxy}-2-methylpropanoate Step A: Methyl 2-{4-[2-(6-benzoyl-2-oxo-1,3-benzothiazol-3(2H)-yl)ethoxy]-phenoxy}-2-methylpropanoate The procedure is as in Step A of Example 31, replacing the ethyl 2-[4-(2-chloroethoxy)phenoxy]-2-methylpropanoate by methyl 2-[4-(2-chloroethoxy)phenoxy]-2-methyl propanoate.

Melting point: 97–98° C.

Step B: Methyl 2-{4-[2-(6-[(methoxyimino)(phenyl)methyl]-2-oxo-1,3-benzothiazol-3(2H)-yl)ethoxy]phenoxy}-2-methylpropanoate Starting from the compound obtained in Step A, the procedure is as in Step B of Example 31.

EXAMPLE 85

Ethyl 2-{3-[2-(6-[(methoxyimino)(phenyl)methyl]-2-oxo-1,3-benzothiazol-3(2H)-yl)ethoxy]phenoxy}-2-methylpropanoate Step A: Ethyl 2-{3-[2-(6-benzoyl-2-oxo-1,3-benzothiazol-3(2H)-yl)ethoxy]phenoxy}-2-methylpropanoate The procedure is as in Step A of Example 31, replacing the 2-[4-(2-chloroethoxy)phenoxy]-2-methylpropanoate by ethyl 2-[3-(2-chloroethoxy)phenoxy]-2-methylpropanoate.

Melting point: 115–116° C.

Step B: Ethyl 2-{3-[2-(6-[(methoxyimino)(phenyl)methyl]-2-oxo-1,3-benzothiazol-3(2H)-yl)ethoxy]phenoxy}-2-methylpropanoate Starting from the compound obtained in Step A, the procedure is as in Step B of Example 31.

EXAMPLE 86

2-{3-[2-(6-[(Methoxyimino)(phenyl)methyl]-2-oxo-1,3-benzothiazol-3(2H)-yl)ethoxy]phenoxy}-2-methylpropanoic acid 1st Method:
Starting from the compound obtained in Example 85, the procedure is as in Example 33.
2nd Method:

Step A: 2-{3-[2-(6-Benzoyl-2-oxo-1,3-benzothiazol-3(2H)-yl)ethoxy]phenoxy}-2-methylpropanoic acid Starting from the compound obtained in Step A of Example 85, the procedure is as in Example 33.
Melting point: 130–13 1° C.

Step B: 2-{3-[2-(6-[(Methoxyimino)(phenyl)methyl]-2-oxo-1,3-benzothiazol-3(2H)-yl)ethoxy]phenoxy}-2-methylpropanoic acid Starting from the compound obtained in Step A, the procedure is as in Step D of Example 1.

EXAMPLE 87

N-Benzoyl-4-[2-(6-[(hydroxyimino)(phenyl)methyl]-2-oxo-1,3-benzothiazol-3(2H1)-yl)ethoxy]phenylalanine 1st Method:
Starting from the compound obtained in Example 17, the procedure is as in Example 33.
2nd Method:

Step A: N-Benzoyl-4-[2-(6-benzoyl-2-oxo-1,3-benzothiazol-3(2H)-yl)ethoxy]phenyl-alanine Starting from the compound obtained in Step A of Example 17, the procedure is as in Example 33.
Melting point: 108–110° C.

Step B: N-Benzoyl-4-[2-(6-[(hydroxyimino)(phenyl)methyl]-2-oxo-1,3-benzothiazol-3(2H)-yl)ethoxy]phenylalanine Starting from the compound obtained in Step A, the procedure is as in Step B of Example 2.

EXAMPLE 88

N-[(Benzyloxy)carbonyl]-4-[2-(6[(hydroxyimino)(phenyl)methyl]-2-oxo-1,3-benzothiazol-3(2H)-yl)ethoxy]phenylalanine 1st Method:
Starting from the compound obtained in Example 14, the procedure is as in Example 33.
2nd Method:

Step A: 4-[2-(6-Benzoyl-2-oxo-1,3-benzothiazol-3(2H)-yl)ethoxy]-N-[(benzyloxy)-carbonyl]phenylalanine Starting from the compound obtained in Step A of Example 14, the procedure is as in Example 33.
Melting point: 74–76° C.

Step B: N-[(Benzyloxy)carbonyl]-4-[2-(6-[(hydroxyimino)(phenyl)methyl]-2-oxo-1,3-benzothiazol-3(2H)-yl)ethoxy]phenylalanine Starting from the compound obtained in Step A, the procedure is as in Step B of Example 2.

EXAMPLE 89

Methyl 3-{4-[2-(6-[(methoxyimino)(phenyl)methyl]-2-oxo-1,3-benzothiazol-3(2H)-yl)ethoxy]phenyl}-2-[(trifluoroacetyl)amino]-propanoate Step A: Methyl 3-{4-[2-(6-benzoyl-2-oxo-1,3-benzothiazol-3(2H)-yl)ethoxy]phenyl}-2-[(trifluoroacetyl)amino]propanoate The procedure is as in Step A of Example 15, replacing the acetyl chloride by trifluoroacetyl chloride.
Melting point: 60–62° C.

Step B: Methyl 3-{4-[2-(6-[(methoxyimino)(phenyl)methyl]-2-oxo-1,3-benzothiazol-3(2H)-yl)ethoxy]phenyl}-2-[(trifluoroacetyl)amino]propanoate Starting from the compound obtained in Step A, the procedure is as in Step B of Example 2.

Pharmacological Study

EXAMPLE A

Acute Toxicity Study

The acute toxicity was evaluated after oral administration to groups each comprising 8 mice (26±2 g). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Efficacy in Genetic Models

Mutations in laboratory animals and also different sensitivities to dietary regimens have allowed the development of animal models having non-insulin dependent diabetes and hyperlipidaemia associated with obesity and with resistance to insulin.

Genetic mice models (ob/ob) (Diabetes, 1982, 31 (1), 1–6) and Zucker (fa/fa) rats have been developed by various laboratories in order to understand the physiopathology of those diseases and test the efficacy of new antidiabetic compounds (Diabetes, 1983, 32, 830–838).

Antidiabetic and Hypolipidaemic Effect in the ob/ob Mouse

The 10-week-old female ob/ob mouse (Harlan) is used for the in vivo tests. The animals are kept in a light-darkness cycle of 12 hours at 25° C. The mouse has a basal hyperglycaemia of 2 g/l. The animals are randomly selected in terms of their glycaemia to form groups of six. The compounds tested by the intraperitoneal route are dissolved in a mixture of dimethyl sulphoxide (10%) and Solutol (15%) to be administered at 10 mg/kg in a volume of 2.5 ml/kg twice per day for four days. By the per os route, the compounds are tested at 30 mg/kg administered in a volume of 2.5 ml/kg of 1% HEC twice per day for four days. The control groups receive the solvents under the same conditions as the treated groups. The activity of the products is evaluated by measuring glycaemia 24 hours after the final administration and by measuring body weight daily.

The compounds of the invention demonstrate a very good capacity to lower glycaemia that is comparable to the effects obtained with rosiglitazone, which is used as reference substance, but with an insignificant change in body weight, whereas under the same conditions rosiglitazone exhibits a significant increase in four days. Furthermore, no side effects were observed during the in vivo tests.

As for an example, compound of Example 3 decrease the glycaemia of 51% compared to the control group, which is comparable to that 61% observed for the Rosiglitazone in the same conditions. Moreover, animals treated with Rosiglitazone show an increase of the body weight of 33% compared to the increase of body weight of the control group, whereas compound of Example 3, in the same conditions show a decrease of 80% of the gain of weight compared to the control group.

EXAMPLE C

Pharmaceutical Composition 1000 tablets each containing 5 mg of the active ingredient Methyl 3-{4-[2-(6-[(methoxyimino)(phenyl)methyl]-2-oxo-1,3-benzothiazol-3(2H)-yl)ethoxy]phenyl}-2-(2,2,2-trifluoroethoxy)propanoate

| | |
|---|---|
| (Example 3) | 5 g |
| wheat starch | 20 g |
| maize starch | 20 g |
| lactose | 30 g |
| magnesium stearate | 2 g |
| silica | 1 g |
| hydroxypropyl cellulose | 2 g |

The invention claimed is:
1. A compound selected from those of formula (I):

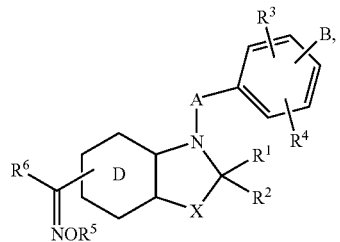

wherein:
X represents oxygen sulfur, or
$R^1$ and $R^2$, together form oxo,
A represents a ethoxy
$R^3$ and $R^4$, which may be the same or different, each represent hydrogen, halogen, R, OR or NRR' wherein R and R', which may be the same or different, each represent hydrogen, linear or branched ($C_1$–$C_6$)alkyl, linear or branched ($C_2$–$C_6$)alkenyl, linear or branched ($C_2$–$C_6$)alkynyl, aryl, aryl-($C_1$–$C_6$)alkyl in which the alkyl moiety is linear or branched, aryl-($C_2$–$C_6$)alkenyl in which the alkenyl moiety is linear or branched, aryl-($C_2$–$C_6$)alkynyl in which the alkynyl moiety is linear or branched, heteroaryl, heteroaryl-($C_1$–$C_6$)alkyl in which the alkyl moiety is linear or branched, heteroaryl-($C_2$–$C_6$)alkenyl in which the alkenyl moiety is linear or branched, heteroaryl-($C_2$–$C_6$)alkynyl in which the alkynyl moiety is linear or branched, ($C_3$–$C_8$)cycloalkyl, ($C_3$–$C_8$)cycloalkyl-($C_1$–$C_6$)alkyl in which the alkyl moiety is linear or branched, or linear or branched ($C_1$–$C_6$)polyhaloalkyl, or $R^3$ and $R^4$, together with the carbon atoms carrying them, when they are carried by two adjacent carbon atoms, form a ring that has 5 or 6 ring members and that may contain a heteroatom selected from oxygen, sulphur and nitrogen, $R^5$ and $R^6$, which may be the same or different, each have the same meanings as R as defined hereinbefore, D represents a benezene nucleus, B represents linear or branched ($C_1$–$C_6$)alkyl or linear or branched ($C_2$–$C_6$)alkenyl, those groups being substituted:

by a group of formula (II):

wherein: —$R^7$ represents

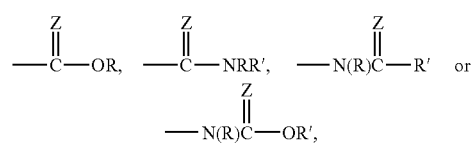

wherein Z represents oxygen or sulphur, and R and R', which may be the same or different are as defined hereinbefore, and $R^8$ represents aryl, arylalkyl wherein the alkyl moiety contains from 1 to 6 carbon atoms and may be linear or branched, heteroaryl, heteroarylalkyl wherein the alkyl moiety contains from 1 to 6 carbon atoms and may be linear or branched, CN, tetrazole, —OR, —NRR',

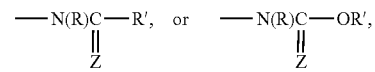

wherein Z is as defined hereinbefore and R and R', which may be the same or different are as defined hereinbefore, or by a group $R^9$, wherein $R^9$ represents CN, tetrazole,

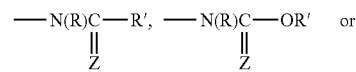

-continued

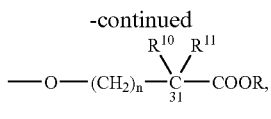

wherein Z is as defined hereinbefore and R and R', which may be the same or different are as defined hereinbefore, n represents 0, 1, 2, 3, 4, 5 or 6, and $R^{10}$ and $R^{11}$, which may be the same or different, each represent hydrogen or linear or branched ($C_1$–$C_6$) alkyl, it being understood that $R^{10}$ and $R^{11}$ cannot simultaneously represent hydrogen, or B represents a group of formula (II) or a group $R^9$ as defined hereinbefore, it being understood that:
- the oxime $R^6$—C(=N—$OR^5$)— may be of Z or E configuration,
- aryl means phenyl, naphthyl or biphenyl, it being possible for those groups to be partially hydrogenated,
- heteroaryl means any mono- or bi-cyclic aromatic group containing 5 to 10 members, which may be partially hydrogenated in one of the rings in the case of bicyclic heteroaryls and which contains 1 to 3 hetero atoms selected from oxygen, nitrogen and sulphur,
- it being possible for the aryl and heteroaryl groups thereby defined to be substituted by 1 or more groups selected from linear or branched ($C_1$–$C_6$)alkyl, linear or branched ($C_1$–$C_6$)polyhaloalkyl, linear or branched ($C_1$–$C_6$)alkoxy, hydroxy, carboxy, formyl, $NR_bR_c$ wherein $R_b$ and $R_c$, which may be the same or different, each represent hydrogen, linear or branched ($C_1$–$C_6$) alkyl, aryl or heteroaryl, ester, amido, nitro, cyano, and halogen,
- its enantiomers and diastereoisomers, and addition salts thereof with a pharmaceutically-acceptable acid or base.

2. A compound according to claim 1, wherein $R^3$ and $R^4$ represent hydrogen.

3. A compound according to claim 1, wherein X represents sulphur.

4. A compound according to claim 1, wherein $R^5$ represents hydrogen.

5. A compound according to claim 1, wherein $R^5$ represents alkyl.

6. A compound according to claim 1, wherein $R^6$ represents unsubstituted phenyl.

7. A compound according to claim 1, wherein $R^6$ represents substituted phenyl.

8. A compound according to claim 1, wherein $R^6$ represents phenyl substituted by halogen.

9. A compound according to claim 1, wherein B represents alkyl substituted by a group

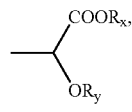

wherein $R_x$ and $R_y$, which may be the same or different, represent hydrogen or ($C_1$–$C_6$) alkyl.

10. A compound according to claim 1, wherein B represents alkyl substituted by a group

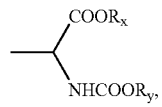

wherein $R_x$ and $R_y$, which may be the same or different, represent hydrogen or ($C_1$–$C_6$) alkyl.

11. A compound according to claim 1, wherein B represents alkyl substituted by a group

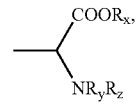

wherein $R_x$, $R_y$ and $R_z$, which may be the same or different, represent hydrogen or ($C_1$–$C_6$) alkyl.

12. A compound according to claim 1, wherein B represents a group

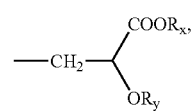

wherein $R_x$ and $R_y$, which may be the same or different, represent hydrogen or ($C_1$–$C_6$) alkyl.

13. A compound according to claim 1, wherein B represents a group

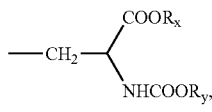

wherein $R_x$ and $R_y$, which may be the same or different, represent hydrogen or ($C_1$–$C_6$) alkyl.

14. A compound according to claim 1, wherein B represents a group

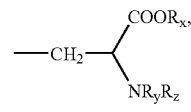

wherein $R_x$, $R_y$ and $R_z$, which may be the same or different, represent hydrogen or ($C_1$–$C_6$) alkyl.

15. A compound according to claim 1 which is selected from:
- Methyl 2-ethoxy-3-{4-[2-(6-[(E)-(methoxyimino)(phenyl)methyl]-2-oxo-1,3-benzothiazol-3(2H)-yl)ethoxy]phenyl} propanoate,
- Methyl 2-ethoxy-3-{4-[2-(6-[(Z)-(hydroxyimino)(phenyl)methyl]-2-oxo-1,3-benzothiazol-3(2H)-yl)ethoxy]phenyl}propanoate,
- Methyl 3-{4-[2-(6-[(methoxyimino)(phenyl)methyl]-2-oxo-1,3-benzothiazol-3(2H)-yl)ethoxy]phenyl}-2-(2,2,2-trifluoroethoxy)propanoate,
- Methyl 3-{4-[2-(6-[(hydroxyimino)(phenyl)methyl]-2-oxo-1,3-benzothiazol-3(2H)-yl)ethoxy]phenyl}-2-(2,2,2-trifluoro-ethoxy)propanoate, 2-Ethoxy-3-{4-[2-(6-[(methoxyimino)(phenyl)methyl]-2-oxo-1,3-benzothiazol-3(2H)-yl)ethoxy]phenyl}propanoic acid,
2-Ethoxy-3-{4-[2-(6-[(E)-(methoxyimino)(phenyl)methyl]-2-oxo-1,3-benzothiazol-3(2H)-yl)ethoxy]phenyl}propanoic acid,
2-Ethoxy-3-{4-[2-(6-[(E)-(methoxyimino)(phenyl)methyl]-2-oxo-1,3-benzothiazol-3(2H)-yl)ethoxy]phenyl}propanoic acid, enantiomer 1,
2-Ethoxy-3-{4-[2-(6-[(E)-(methoxyimino)(phenyl)methyl]-2-oxo-1,3-benzothiazol-3(2H)-yl)ethoxy]phenyl}propanoic acid, enantiomer 2,
2-Ethoxy-3-{4-[2-(6-[(Z)-(methoxyimino)(phenyl)methyl]-2-oxo-1,3-benzothiazol-3(2H)-yl)ethoxy]phenyl}propanoic acid,
2-Ethoxy-3-{4-[2-(6-[(Z)-(methoxyimino)(phenyl)methyl]-2-oxo-1,3-benzothiazol-3(2H1)-yl)ethoxy]phenyl}propanoic acid, enantiomer 1,
2-Ethoxy-3-{4-[2-(6-[(Z)-(methoxyimino)(phenyl)methyl]-2-oxo-1,3-benzothiazol-3(2H)-yl)ethoxy]phenyl}propanoic acid, enantiomer 2,
2-Ethoxy-3-{4-[2-(6-[(hydroxyimino)(phenyl)methyl]-2-oxo-1,3-benzothiazol-3(2H)-yl)ethoxy]phenyl}propanoic acid,
Methyl 3-{4-[2-(6-[(Z)-(3-chlorophenyl)(methoxyimino)methyl]-2-oxo-1,3-benzothiazol-3(2H)-yl)ethoxy]phenyl}-2-ethoxypropanoate,
Methyl 3-{4-[2-(6-[(3-chlorophenyl)(hydroxyimino)methyl]-2-oxo-1,3-benzothiazol-3(2H)-yl)ethoxy]phenyl}-2-ethoxypropanoate,
Methyl 2-methoxy-3-{4-[2-(6-[(methoxyimino)(phenyl)methyl]-2-oxo-1,3-benzothiazol-3(2H)-yl)ethoxy]phenyl}propanoate,
3-{4-[2-(6-[(Z)-(3-chlorophenyl)(methoxyimino)methyl]-2-oxo-1,3-benzothiazol-3(2H)-yl)ethoxy]phenyl}-2-ethoxypropanoic acid,
3-{4-[2-(6-[(methoxyimino)(phenyl)methyl]-2-oxo-1,3-benzothiazol-3(2H)-yl)ethoxy]phenyl}-2-(2,2,2-trifluoroethoxy)propanoic acid,
3-{4-[2-(6-[(E)-(methoxyimino)(phenyl)methyl]-2-oxo-1,3-benzothiazol-3(2H)-yl)ethoxy]phenyl}-2-(2,2,2-trifluoroethoxy)propanoic acid,
3-{4-[2-(6-[(E)-(methoxyimino)(phenyl)methyl]-2-oxo-1,3-benzothiazol-3(21H)-yl)ethoxy]phenyl}-2-(2,2,2-trifluoroethoxy)propanoic acid, enantiomer 1,
3-{4-[2-(6-[(E)-(methoxyimino)(phenyl)methyl]-2-oxo-1,3-benzothiazol-3(2H)-yl)ethoxy]phenyl}-2-(2,2,2-trifluoroethoxy)propanoic acid, enantiomer 2,
33-{(4-[2-(6-[(Z)-(methoxyimino)(phenyl)methyl]-2-oxo-1,3-benzothiazol-3(2H)-yl)ethoxy]phenyl}-2-(2,2,2-trifluoroethoxy)propanoic acid,
3-{4-[2-(6-[(Z)-(methoxyimino)(phenyl)methyl]-2-oxo-1,3-benzothiazol-3(2H)-yl)ethoxy]phenyl}-2-(2,2,2-trifluoroethoxy)propanoic acid, enantiomer 1,
3-{4-[2-(6-[(Z)-(methoxyimino)(phenyl)methyl]-2-oxo-1,3-benzothiazol-3 (2H)-yl)ethoxy]phenyl}-2-(2,2,2-trifluoroethoxy)propanoic acid, enantiomer 2, and
3-{4-[2-(6-[(tert-Butoxyimino)(phenyl)methyl]-2-oxo-1,3-benzothiazol-3(2H)-yl)ethoxy]phenyl}-2-ethoxypropanoic acid,
its enantiomers and diastereoisomers, and addition salts thereof with a pharmaceutically-acceptable acid or base.

16. A compound according to claim 1 which is selected from:
Methyl 2-[(tert-butoxycarbonyl)amino]-3-{4-[2-(6-[(methoxyimino)(phenyl)methyl]-2-oxo-1,3-benzothiazol-3(2H)-yl)ethoxy]phenyl}propanoate,
Methyl 2-[(tert-butoxycarbonyl)amino]-3-{4-[2-(6-[(hydroxyimino)(phenyl)methyl]-2-oxo-1,3-benzothiazol-3(2H)-yl)ethoxy]phenyl} propanoate,
Methyl 2-[(butoxycarbonyl)amino]-3-{4-[2-(6-[(methoxyimino) (phenyl)methyl]-2-oxo-1,3-benzothiazol-3(2H)-yl)ethoxy]phenyl}propanoate,
Methyl 3-{4-[2-(6-[(methoxyimino)(phenyl)methyl]-2-oxo-1,3-benzothiazol-3(2H)-yl)ethoxy]phenyl}-2-[(phenoxycarbonyl)amino]propanoate,
Methyl 2-{[(benzyloxy)carbonyl]amino}-3-{4-[2-(6-[(hydroxyimino) (phenyl)methyl]-2-oxo-1,3-benzothiazol-3(2H)-yl)ethoxy]phenyl}propanoate,
Methyl 2-[(tert-butoxycarbonyl)(methyl)amino]-3-{4-[2-(6-[(methoxyimino) (phenyl)methyl]-2-oxo-1,3-benzothiazol-3(2H)-yl)ethoxy]phenyl}propanoate,
N-(tert-butoxycarbonyl)-4-[2-(6-[(hydroxyimino)(phenyl)methyl]-2-oxo-1,3-benzothiazol-3(2H)-yl)ethoxy] phenylalanine, and
N-(tert-butoxycarbonyl)-4-[2-(6-[(methoxyimino)(phenyl)methyl]-2-oxo-1,3-benzothiazol-3(2H)-yl)ethoxy] phenylalanine,
its enantiomers and diastereoisomers, and addition salts thereof with a pharmaceutically-acceptable acid or base.

17. A compound according to claim 1 which is selected from:
Methyl 2-amino-3-{4-[2-(6-[(methoxyimino)(phenyl)methyl]-2-oxo-1,3-benzothiazol-3(2H)-yl)ethoxy]phenyl} propanoate,
Methyl 2-amino-3-{4-[2-(6-[(hydroxyimino)(phenyl)methyl]-2-oxo-1,3-benzothiazol-3(2H)-yl)ethoxy]phenyl}propanoate, and
Methyl 3-{4-[2-(6-[(methoxyimino) (phenyl)methyl]-2-oxo-1,3-benzothiazol-3(2H)-yl)ethoxy]phenyl}-2-(methylamino)propanoate,
its enantiomers and diastereoisomers, and addition salts thereof with a pharmaceutically-acceptable acid or base.

18. A compound selected from those of formula (V):

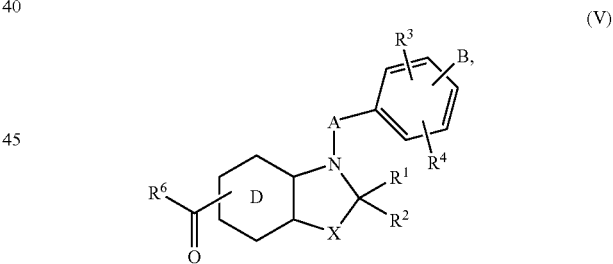

wherein $R^6$, D, X, A, $R^1$, $R^2$, $R^3$, $R^4$ and B are as defined in claim 1, for use as intermediates for the synthesis of compounds of formula I.

19. A method for treating a living animal body, including a human, afflicted with a condition selected from hyperglycemia and non-insulin dependent type II diabetes, comprising the step of administering to the living animal body, including a human, an amount of a compound of claim 1 which is effective for alleviation of the condition.

20. A pharmaceutical composition useful in the method as claimed in claim 16 comprising as active principle an effective amount of a compound of claim 1, together with one or more pharmaceutically-acceptable excipients or vehicles.

* * * * *